United States Patent
Meerpoel et al.

(10) Patent No.: US 8,772,494 B2
(45) Date of Patent: Jul. 8, 2014

(54) N-ARYL PIPERIDINE SUBSTITUTED BIPHENYLCARBOXAMIDES AS INHIBITORS OF APOLIPOPROTEIN B

(75) Inventors: Lieven Meerpoel, Beerse (BE); Marcel Viellevoye, Breda (NL); Joannes Theodorus Maria Linders, Beerse (BE)

(73) Assignee: Janssen Pharmaceutica N.V., Beerse (BE)

( * ) Notice: Subject to any disclaimer, the term of this patent is extended or adjusted under 35 U.S.C. 154(b) by 1937 days.

(21) Appl. No.: 10/580,530

(22) PCT Filed: Dec. 6, 2004

(86) PCT No.: PCT/EP2004/053280
§ 371 (c)(1),
(2), (4) Date: May 24, 2006

(87) PCT Pub. No.: WO2005/058824
PCT Pub. Date: Jun. 30, 2005

(65) Prior Publication Data
US 2007/0099934 A1    May 3, 2007

(30) Foreign Application Priority Data
Dec. 9, 2003 (EP) .................................. 03104601.4

(51) Int. Cl.
*C07D 211/22* (2006.01)
*A61K 31/451* (2006.01)

(52) U.S. Cl.
USPC ........... 546/227; 546/194; 546/229; 514/318; 514/331

(58) Field of Classification Search
USPC ........... 546/239, 194, 227, 229; 514/318, 331
See application file for complete search history.

(56) References Cited

U.S. PATENT DOCUMENTS

| | | | |
|---|---|---|---|
| 6,552,022 B1 * | 4/2003 | Daugan | 514/252.11 |
| 2006/0040989 A1 * | 2/2006 | Meerpoel et al. | 514/333 |

FOREIGN PATENT DOCUMENTS

| WO | WO 0032582 A1 * | 6/2000 |
|---|---|---|
| WO | WO 01/96327 A1 | 12/2001 |
| WO | WO 0197810 A2 * | 12/2001 |
| WO | WO 02/081460 A1 | 10/2002 |
| WO | WO 03/048121 A1 | 6/2003 |

OTHER PUBLICATIONS

Williams et. al. "Novel Microsomal Triglyceride Transfer Protein Inhibitors" Expert Opinion on Therapeutic Patents 2003, 13, 479-488.*
PCT International Search Report dated Oct. 27, 2005 for PCT Application. No. PCT/EP2004/053280 which relates to U.S. Patent Application filed herewith.
Written Opinion of the International Searching Authority for PCT Application No. PCT/EP2004/053280.
Chan et al., "New N- and O-Arylations with Phenylboronic Acids and Cupric Acetate.", Tetrahedron Letters, 1998, vol. 39, pp. 2933-1936, Elsevier Science Ltd.
Sharp et al., "Cloning and gene defects in microsomal triglyceride transfer protein associated with abetalipoproteinemia.", Letters to Nature, 1993, vol. 365, pp. 65-69.
Wetterau et al., "Purification and characterization of microsomal triglyceride and cholesteryl ester transfer protein from bovine liver microsomes.", Chemistry and Physics of Lipids, 1985, vol. 38, pp. 205-222.
Willoughby et al., "Solid Phase Synthesis of Aryl Amines.", Tetrahedron Letters, 1996, vol. 37(40) pp. 7181-7184, Elsevier Science Ltd.
Wolfe et al., "An Improved Catalyst System for Aromatic Carbon-Nitrogen Bond Formation: The Possible Involvement of Bis(Phosphine) Palladium Complexes as Key Intermediates.", J. Am.Chem. Soc., 1996, vol. 118, pp. 7215-7216.

* cited by examiner

*Primary Examiner* — David K O Dell

(57) ABSTRACT

N-aryl piperidine substituted biphenylcarboxamides compounds of formula (I)

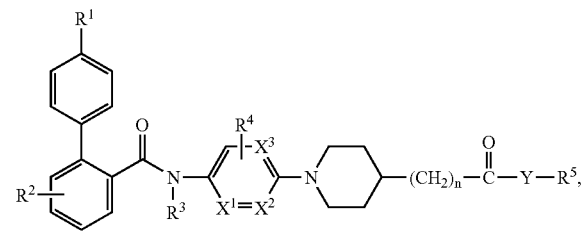

methods for preparing such compounds, pharmaceutical compositions comprising said compounds as well as the use of said compounds as a medicine for the treatment of hyperlipidemia, obesity and type II diabetes.

8 Claims, No Drawings

N-ARYL PIPERIDINE SUBSTITUTED BIPHENYLCARBOXAMIDES AS INHIBITORS OF APOLIPOPROTEIN B

CROSS REFERENCE TO RELATED APPLICATIONS

This application is the US national stage of Application No. PCT/EP2004/053280, filed Dec. 6, 2004, which application claims priority from EP 03104601.4, filed Dec. 9, 2003.

The present invention is concerned with novel N-aryl piperidine substituted biphenylcarboxamide compounds having apolipoprotein B inhibiting activity and concomitant lipid lowering activity. The invention further relates to methods for preparing such compounds, pharmaceutical compositions comprising said compounds as well as the use of said compounds as a medicine for the treatment of hyperlipidemia, obesity and type II diabetes.

Obesity is the cause of a myriad of serious health problems like the adult onset of diabetes and heart disease. In addition, the loss of weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia.

Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis inhibitors such as HMG Co-enzyme-A reductase inhibitors. There still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of a coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, so named because it appears to be about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolaemia, familial combined hyperlipidaemia, familial hypercholesterolaemia, remnant hyperlipidaemia, chylomicronaemia syndrome and familial hyper-triglyceridaemia.

Microsomal triglyceride transfer protein (hereinafter referred as MTP) is known to catalyze the transport of triglyceride and cholesteryl ester by preference to phospholipids such as phosphatidylcholine. It was demonstrated by D. Sharp et al., Nature (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans.

One of the goals of the present invention is to provide an improved treatment for patients suffering from obesity or atherosclerosis, especially coronary atherosclerosis and more generally from disorders which are related to atherosclerosis, such as ischaemic heart disease, peripheral vascular disease and cerebral vascular disease. Another goal of the present invention is to cause regression of atherosclerosis and inhibit its clinical consequences, particularly morbidity and mortality.

MTP inhibitors have been disclosed in WO-00/32582, WO-01/96327 and WO-02/20501.

The present invention is based on the unexpected discovery that a class of novel N-aryl piperidine substituted biphenylcarboxamide compounds is acting as selective MTP inhibitors, i.e. is able to selectively block MTP at the level of the gut wall in mammals, and is therefore a promising candidate as a medicine, namely for the treatment of hyperlipidemia. The present invention additionally provides several methods for preparing such N-aryl piperidine substituted biphenylcarboxamide compounds, as well as pharmaceutical compositions including such compounds. Furthermore, the invention provides a certain number of novel compounds which are useful intermediates for the preparation of the therapeutically active N-aryl piperidine substituted biphenyl-carboxamide compounds, as well as methods for preparing such intermediates. Finally, the invention provides a method of treatment of a condition selected from atherosclerosis, pancreatitis, obesity, hypercholesterolemia, hypertriglyceridemia, hyperlipidemia, diabetes and type II diabetes, comprising administering a therapeutically active amount of a compound of formula (I) to a mammal.

The present invention relates to a family of novel compounds of formula (I)

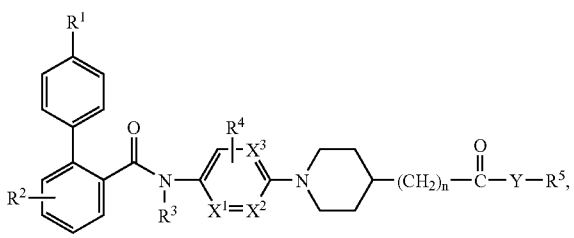

(I)

the N-oxides, the pharmaceutically acceptable acid addition salts and the stereochemically isomeric forms thereof, wherein $R^1$ is hydrogen, $C_{1-4}$alkyl, halo, or polyhalo$C_{1-4}$alkyl;
$R^2$ is hydrogen, $C_{1-4}$alkyl, halo, or polyhalo$C_{1-4}$alkyl;
$R^3$ is hydrogen or $C_{1-4}$alkyl;
$R^4$ is hydrogen, $C_{1-4}$alkyl, or halo;
n is an integer 0, or 1;
$X^1$ is carbon and $X^2$ is carbon; or $X^1$ is nitrogen and $X^2$ is carbon;
or $X^1$ is carbon and $X^2$ is nitrogen;
$X^3$ is carbon or nitrogen;
Y represents O, or $NR^6$ wherein $R^6$ is hydrogen or $C_{1-4}$alkyl;
$R^5$ represents a radical of formula

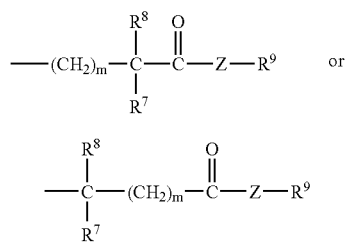

wherein
m is an integer 0, 1, or 2;
Z is O or NH;
$R^7$ is hydrogen;
  $C_{1-6}$alkyl;
  $C_{1-6}$alkyl substituted with hydroxy, amino, mono- or di($C_{1-4}$alkyl)amino,
  $C_{1-4}$alkyloxycarbonyl, aminocarbonyl, aryl or heteroaryl;
  $C_{1-4}$alkyl-O—$C_{1-4}$alkyl;
  $C_{1-4}$alkyl-S—$C_{1-4}$alkyl; or aryl;
$R^8$ is hydrogen of $C_{1-4}$alkyl;
$R^9$ is hydrogen, $C_{1-4}$alkyl, aryl$^1$, or $C_{1-4}$alkyl substituted with aryl$^1$;
or when Y represents $NR^6$ the radicals $R^5$ and $R^6$ may be taken together with the nitrogen to which they are attached to form pyrrolidinyl substituted with $C_{1-4}$alkyloxycarbonyl and optionally further substituted with hydroxy; or piperidinyl substituted with $C_{1-4}$alkyloxycarbonyl;
aryl is phenyl; phenyl substituted with one, two or three substituents each independently selected from $C_{1-4}$alkyl, $C_{1-4}$alkyloxy, halo, hydroxy, nitro, cyano, $C_{1-4}$alkyloxycarbonyl, trifluoromethyl, or trifluoromethoxy; or benzo[1,3]dioxolyl;
aryl$^1$ is phenyl; phenyl substituted with one, two or three substituents each independently selected from $C_{1-4}$alkyl, $C_{1-4}$alkyloxy, halo, hydroxy, nitro, cyano, $C_{1-4}$alkyloxycarbonyl, trifluoromethyl, or trifluoromethoxy; and heteroaryl is imidazolyl, thiazolyl, indolyl, or pyridinyl.

Unless otherwise stated, as used in the foregoing definitions and hereinafter:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, n-butyl, 1-methylethyl, 2-methylpropyl, 1,1-dimethylethyl and the like;
$C_{1-6}$alkyl is meant to include $C_{1-4}$alkyl (as hereinabove defined) and the higher homologues thereof having 5 or 6 carbon atoms, such as for instance 2-methylbutyl, n-pentyl, dimethylpropyl, n-hexyl, 2-methylpentyl, 3-methylpentyl and the like;
polyhalo$C_{1-4}$alkyl is defined as $C_{1-4}$alkyl substituted with 2 to 6 halogen atoms such as difluoromethyl, trifluoromethyl, trifluoroethyl, and the like;
$C_{1-4}$alkylamino defines secondary amino radicals having from 1 to 4 carbon atoms such as, for example, methylamino, ethylamino, propylamino, isopropylamino, butylamino, isobutylamino and the like;
di($C_{1-4}$alkyl)amino defines tertiary amino radicals having from 1 to 4 carbon atoms such as, for example, dimethylamino, diethylamino, dipropylamino, diisopropylamino, N-methyl-N'-ethylamino, N-ethyl-N'-propylamino and the like.

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of formula (I) wherein a nitrogen atom is oxidized to the N-oxide. In particular said N-oxide forms are compounds of formula (I) wherein the nitrogen of the piperidinyl group is oxidized.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

The terms cis and trans are used herein in accordance with Chemical Abstracts nomenclature and refer to the position of the substituents on a ring moiety.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

In an embodiment the present invention concerns the compounds of formula (I), the N-oxides, the pharmaceutically acceptable acid addition salts and the stereochemically isomeric forms thereof, wherein
$R^1$ is hydrogen, $C_{1-4}$alkyl, halo, or polyhalo$C_{1-4}$alkyl;
$R^2$ is hydrogen, $C_{1-4}$alkyl, halo, or polyhalo$C_{1-4}$alkyl;
$R^3$ is hydrogen or $C_{1-4}$alkyl;
$R^4$ is hydrogen, $C_{1-4}$alkyl, or halo;
n is an integer 0, or 1;
$X^1$ is carbon and $X^2$ is carbon; or $X^1$ is nitrogen and $X^2$ is carbon;
or $X^1$ is carbon and $X^2$ is nitrogen;
$X^3$ is carbon or nitrogen;
Y represents O, or $NR^6$ wherein $R^6$ is hydrogen or $C_{1-4}$alkyl;
$R^5$ represents a radical of formula $$-(CH_2)_m-\underset{R^7}{\overset{R^8}{\underset{|}{\overset{|}{C}}}}-\overset{O}{\overset{\|}{C}}-Z-R^9 \qquad (a\text{-}1)$$

$$-\underset{R^7}{\overset{R^8}{\underset{|}{\overset{|}{C}}}}-(CH_2)_m-\overset{O}{\overset{\|}{C}}-Z-R^9 \qquad (a\text{-}2)$$

wherein
m is an integer 0, 1, or 2;
Z is O or NH;
$R^7$ is hydrogen;
   $C_{1-6}$alkyl;
   $C_{1-6}$alkyl substituted with hydroxy, amino, mono- or di($C_{1-4}$alkyl)amino,
   $C_{1-4}$alkyloxycarbonyl, aminocarbonyl, aryl or heteroaryl;
   $C_{1-4}$alkyl-O—$C_{1-4}$alkyl;
   $C_{1-4}$alkyl-S—$C_{1-4}$alkyl; or aryl;
$R^8$ is hydrogen of $C_{1-6}$alkyl;
$R^9$ is $C_{1-6}$alkyl, phenyl or benzyl;
or when Y represents $NR^6$ the radicals $R^5$ and $R^6$ may be taken together with the nitrogen to which they are attached to form pyrrolidinyl substituted with $C_{1-4}$alkyloxycarbonyl and optionally further substituted with hydroxy; or piperidinyl substituted with $C_{1-4}$alkyloxycarbonyl;
aryl is phenyl; phenyl substituted with one, two or three substituents each independently selected from $C_{1-4}$alkyl, $C_{1-4}$alkyloxy, halo, hydroxy, nitro, cyano, $C_{1-4}$alkyloxycarbonyl, trifluoromethyl, or trifluoromethoxy; or benzo[1,3]dioxolyl; and
heteroaryl is imidazolyl, thiazolyl, indolyl, or pyridinyl.

In another embodiment the present invention concerns compounds of formula (I) the N-oxides, the pharmaceutically acceptable acid addition salts and the stereochemically isomeric forms thereof, wherein
$R^1$ is polyhalo$C_{1-4}$alkyl;
$R^2$ is hydrogen, or $C_{1-4}$alkyl;
$R^3$ is hydrogen or $C_{1-4}$alkyl;
$R^4$ is hydrogen;
n is an integer 0, or 1;
$X^1$ is carbon and $X^2$ is carbon; or $X^1$ is nitrogen and $X^2$ is carbon;
or $X^1$ is carbon and $X^2$ is nitrogen;
$X^3$ is carbon or nitrogen;
Y represents O, or $NR^6$ wherein $R^6$ is hydrogen or $C_{1-4}$alkyl;
$R^5$ represents a radical of formula $$-\underset{R^7}{\overset{R^8}{\underset{|}{\overset{|}{C}}}}-(CH_2)_m-\overset{O}{\overset{\|}{C}}-Z-R^9 \qquad (a\text{-}2)$$

wherein
m is an integer 0, or 1;
Z is O or NH;
$R^7$ is hydrogen; $C_{1-6}$alkyl; $C_{1-6}$alkyl substituted with amino,
   $C_{1-4}$alkyloxycarbonyl, aryl or heteroaryl; $C_{1-4}$alkyl-S—$C_{1-4}$alkyl; or aryl;
$R^8$ is hydrogen of $C_{1-6}$alkyl;
$R^9$ is $C_{1-4}$alkyl;
or when Y represents $NR^6$ the radicals $R^5$ and $R^6$ may be taken together with the nitrogen to which they are attached to form pyrrolidinyl substituted with $C_{1-4}$alkyloxycarbonyl and optionally further substituted with hydroxy; or piperidinyl substituted with $C_{1-4}$alkyloxycarbonyl;
aryl is phenyl; phenyl substituted with hydroxy; or benzo[1,3]dioxolyl;
heteroaryl is imidazolyl.

A group of interesting compounds consists of those compounds of formula (I) wherein one or more of the following restrictions apply:
a) $R^1$ is tert-butyl or trifluoromethyl;
b) $R^2$ is hydrogen or $C_{1-4}$alkyl;
c) $R^3$ is hydrogen;
d) $R^4$ is hydrogen;
e) Y represents $NR^6$ wherein $R^6$ is hydrogen or methyl;
f) Z represents O;
g) $R^8$ represents hydrogen;
h) $R^9$ represents $C_{1-4}$alkyl.

A first particular group of compounds are those compounds of formula (I) wherein $X^1$, $X^2$ and $X^3$ are carbon.

A second particular group of compounds are those compounds of formula (I) wherein $X^1$ is carbon, $X^2$ is nitrogen, and $X^3$ is carbon.

A third particular group of compounds are those compounds of formula (I) wherein $X^1$ is nitrogen, $X^2$ is carbon, and $X^3$ is carbon.

A fourth particular group of compounds are those compounds of formula (I) wherein $X^1$ is carbon, $X^2$ is nitrogen, and $X^3$ is nitrogen.

A fifth particular group of compounds are those compounds of formula (I) wherein n is the integer 1.

A first preferred group of compounds are those compounds of formula (I) wherein $R^1$ is trifluoromethyl; $R^2$ is hydrogen; $R^3$ is hydrogen; $R^4$ is hydrogen; $X^1$, $X^2$ and $X^3$ are carbon; n is the integer 1; Y represents $NR^6$ wherein $R^6$ is hydrogen or methyl; and $R^5$ is a radical of formula (a-1) wherein m is the integer 0.

A second preferred group of compounds are those compounds of formula (I) wherein $R^1$ is trifluoromethyl; $R^2$ is hydrogen; $R^3$ is hydrogen; $R^4$ is hydrogen; $X^1$, $X^2$ and $X^3$ are carbon; n is the integer 1; Y represents $NR^6$ wherein $R^6$ is hydrogen or methyl; and $R^5$ is a radical of formula (a-1) wherein m is the integer 1.

A third preferred group of compounds are those compounds of formula (I) wherein $R^1$ is trifluoromethyl; $R^2$ is hydrogen; $R^3$ is hydrogen; $R^4$ is hydrogen; $X^1$, $X^2$ and $X^3$ are carbon; n is the integer 1; Y represents $NR^6$ wherein $R^6$ is hydrogen or methyl; and $R^5$ is a radical of formula (a-2) wherein m is the integer 1.

A fourth preferred group of compounds are those compounds of formula (I) wherein $R^1$ is trifluoromethyl; $R^2$ is hydrogen; $R^3$ is hydrogen; $R^4$ is hydrogen; $X^1$, $X^2$ and $X^3$ are carbon; n is the integer 1; Y represents $NR^6$ and $R^5$ and $R^6$ are taken together with the nitrogen to which they are attached to form pyrrolidinyl substituted with $C_{1-4}$alkyl-oxycarbonyl and optionally further substituted with hydroxy, or piperidinyl substituted with $C_{1-4}$alkyloxycarbonyl.

Particular groups of compounds are those preferred groups of compounds wherein $R^8$ represents hydrogen and $R^9$ represents $C_{1-4}$alkyl.

A first process for preparing compounds of formula (I) is a process wherein an intermediate of formula (II)

(II)

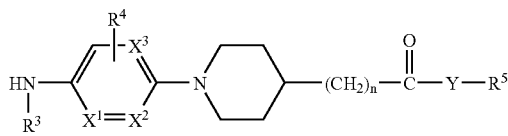

wherein $R^3$, $R^4$, $R^5$, Y, n, $X^1$, $X^2$ and $X^3$ are as defined in formula (I), is reacted with a biphenylcarboxylic acid or halide having the formula (III), (III)

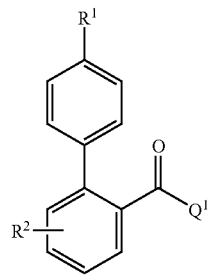

wherein $R^1$ and $R^2$ are as defined in formula (I) and $Q^1$ is selected from hydroxy and halo, in at least one reaction-inert solvent and optionally in the presence of a suitable base, the said process further optionally comprising converting a compound of formula (I) into an addition salt thereof, and/or preparing stereochemically isomeric forms thereof. In case Q1 is hydroxy, it may be convenient to activate the biphenylcarboxylic acid of formula (III) by adding an effective amount of a reaction promoter. Non-limiting examples of such reaction promoters include carbonyldiimidazole, diimides such as N,N'-dicyclohexylcarbodiimide (DCC) or 1-ethyl-3-(3'-dimethylaminopropyl)-carbodiimide (EDCI), and functional derivatives thereof. For this type of acylation procedure, it is preferred to use a polar aprotic solvent such as, for instance, dichloromethane. Suitable bases for carrying out this first process include tertiary amines such as triethylamine, triisopropylamine and the like. Suitable temperatures for carrying out the first process of the invention typically range from about 20° C. to about 140° C., depending on the particular solvent used, and will most often be the boiling temperature of the said solvent.

A second process for preparing compound of the present invention is a process wherein an intermediate having the formula (IV)

(IV)

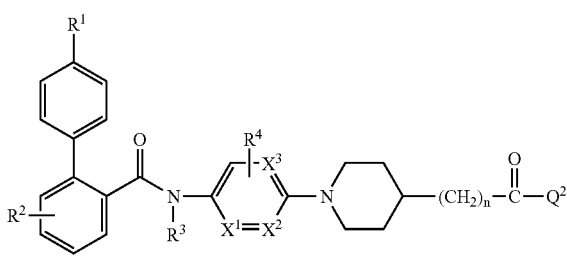

wherein $R^1$, $R^2$, $R^3$, $R^4$, n, $X^1$, $X^2$ and $X^3$ are as defined in formula (I) and $Q^2$ is selected from halo and hydroxy, is reacted with an intermediate (V) of the formula $H-NR^5R^6$, wherein $R^5$ and $R^6$ are as defined for compounds of formula (I), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof. In case $Q^2$ is hydroxy, it may be convenient to activate the carboxylic acid of formula (IV) by adding an effective amount of a reaction promoter. Non-limiting examples of such reaction promoters include carbonyl-diimidazole, diimides such as DCC, EDCI, hydroxybenzotriazole, benzotriazol-1-yl-N-oxytris-(dimethylamino)phosphonium hexafluorophosphate (BOP), tetrapyrrolidino-phosphonium hexafluorophosphate, bromotripyrrolidinophosphonium hexafluorophosphate, or a functional derivative thereof, such as disclosed in "Solid-Phase Synthesis: A Practical Guide", edited by Steven A. Kates and Fernando Albericio, Marcel Dekker, Inc., 2000 (ISBN: 0-8247-0359-6) on pages 306 to 319.

A third process for preparing a compound according to the present invention is a process wherein an intermediate having the formula (VI)

(VI)

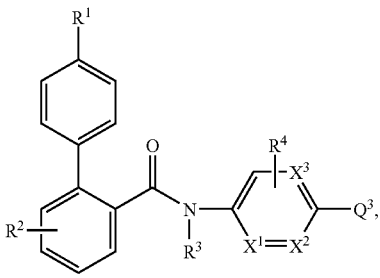

wherein $R^1$, $R^2$, $R^3$, $R^4$, $X^1$, $X^2$ and $X^3$ are as defined in formula (I) and $Q^3$ is selected from halo, $B(OH)_2$, alkylboronates and cyclic analogues thereof, is reacted with a reactant having the formula (VII)

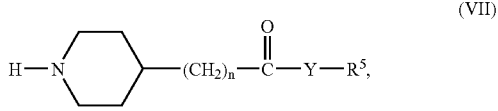

(VII)

wherein n, $R^5$ and Y are as defined in formula (I), in at least one reaction-inert solvent and optionally in the presence of at least one transition metal coupling reagent and/or at least one suitable ligand, the said process further optionally comprising converting a compound of formula (I) into an addition salt thereof, and/or preparing stereochemically isomeric forms thereof. This type of reaction being known in the art as the Buchwald reaction, reference to the applicable metal coupling reagents and/or suitable ligands, e.g. palladium compounds such as palladium tetra(triphenyl-phosphine), tris(dibenzylidene-acetone dipalladium, 2,2'-bis(diphenylphosphino)-1,1'-binaphtyl (BINAP) and the like, may be found for instance in *Tetrahedron Letters*, (1996), 37(40), 7181-7184 and *J. Am. Chem. Soc.*, (1996), 118:7216. If $Q^3$ is $B(OH)_2$, an alkylboronate or a cyclic analogue thereof, then cupric acetate should be used as the coupling reagent, according to *Tetrahedron Letters*, (1998), 39:2933-6.

Compounds of formula (I-a), defined as compounds of formula (I) wherein Y represent NH and $R^3$ represents hydrogen, can conveniently be prepared using solid phase synthesis techniques as depicted in Scheme 1 below. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry are described in for example "Handbook of Combinatorial Chemistry Drugs, Catalysts, Materials" edited by K. C. Nicolaou, R. Hanko, and W. Hartwig, volumes 1 and 2, Wiley (ISBN: 3-527-30509-2).

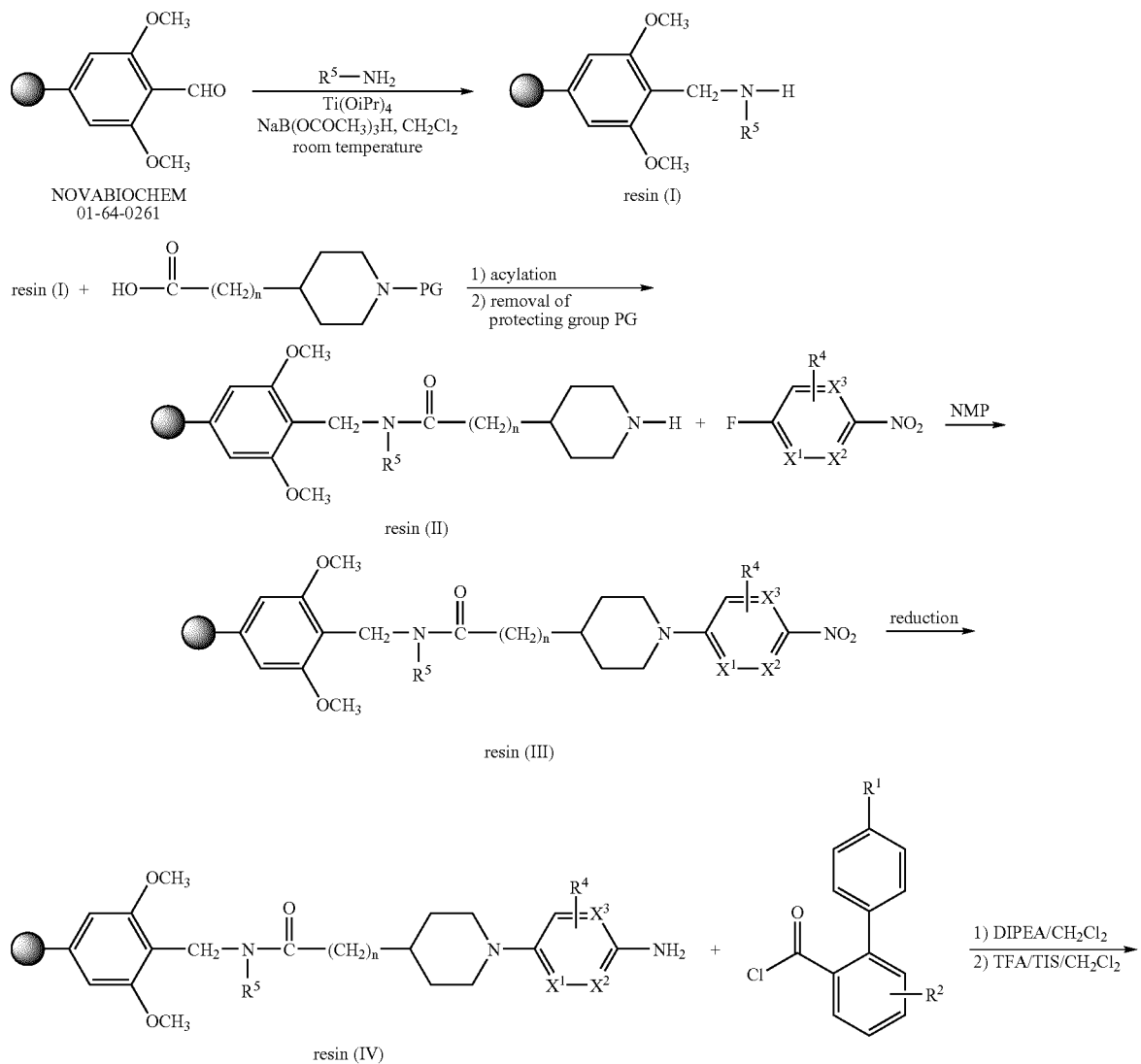

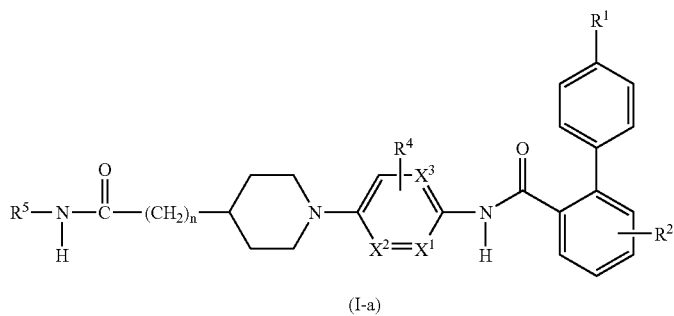

(I-a)

The substituents $R^1$, $R^2$, $R^4$, $R^4$, $R^5$, n, $X^1$, $X^2$ and $X^3$ are as defined for compounds of formula (I). PG represents a protecting group such as, e.g. $C_{1-6}$alkyloxycarbonyl, phenylmethyloxycarbonyl, t-butoxycarbonyl, 9-fluorenylmethoxycarbonyl (Fmoc) and the like. The following abbreviations are used: "NMP" means N-methyl-2-pyrrolidone, "DIPEA" means diisopropylethylamine, "TFA" means trifluoroacetic acid; and "TIS" means triisopropylsilane.

Compounds of formula (I-b), defined as compounds of formula (I) wherein $R^3$ represents hydrogen, may be prepared using a solid phase synthesis route as outlined in Scheme 2.

Scheme 2:

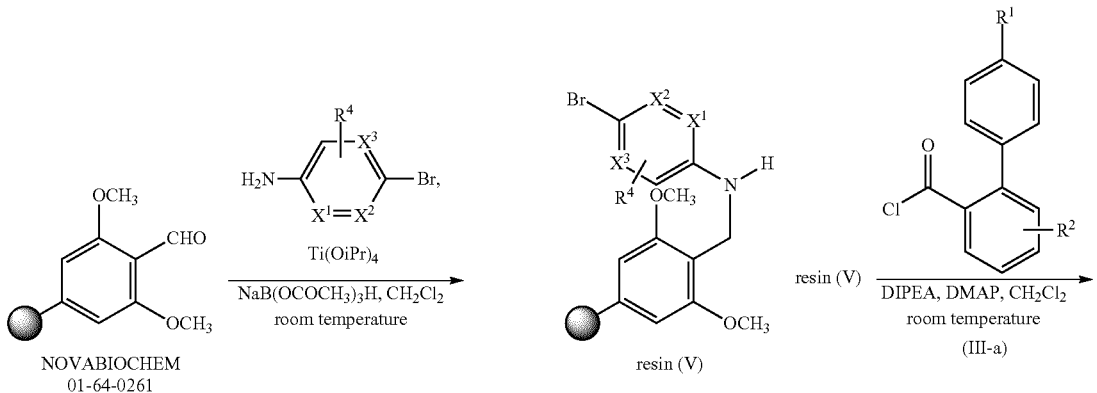

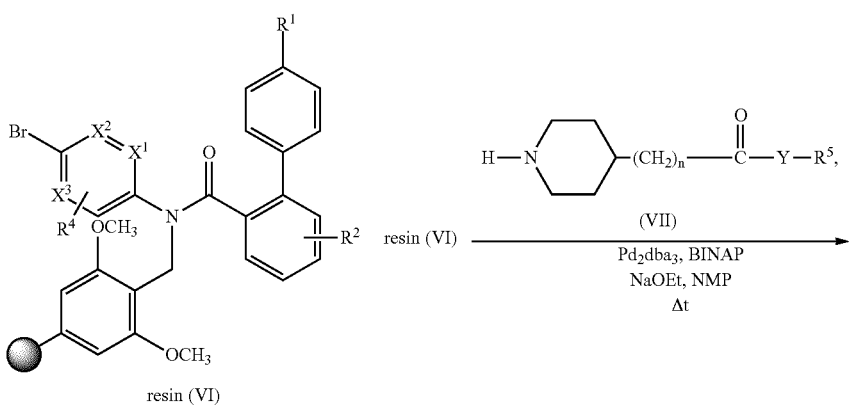

-continued

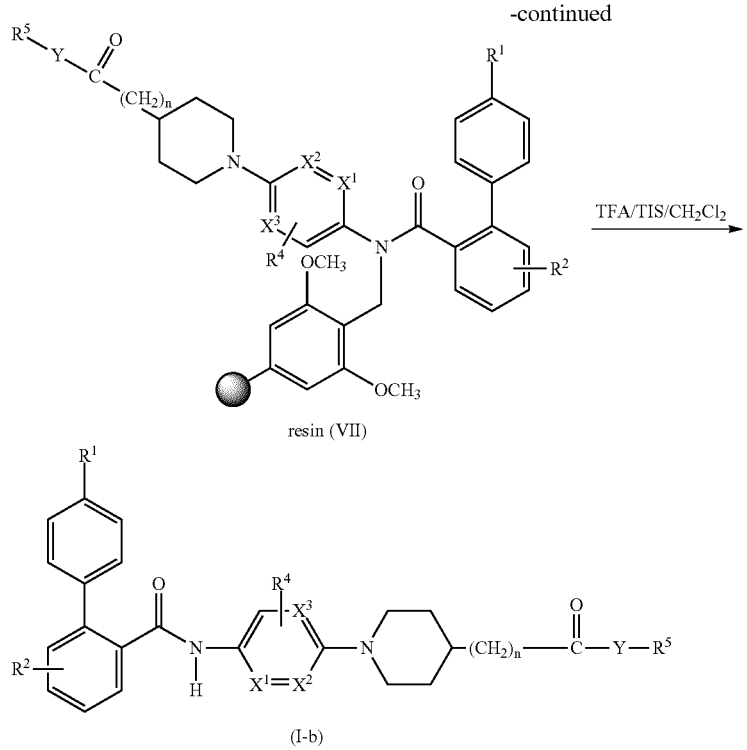

resin (VII)

(I-b)

The substituents $R^1$, $R^2$, $R^4$, $R^4$, $R^5$, Y, n, $X^1$, $X^2$ and $X^3$ are as defined for compounds of formula (I). The following abbreviations are used: "NMP" means N-methyl-2-pyrrolidone, "DIPEA" means diisopropylethylamine, "TFA" means trifluoroacetic acid, "TIS" means triisopropylsilane, "DMAP" means dimethylaminopyridine, and "BINAP" means 2,2'-bis(diphenylphosphino)-1,1'-binaphtyl.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable salts and stereoisomeric forms thereof possess favourable apolipoprotein B inhibiting activity and concomitant lipid lowering activity. Therefore the present compounds of formula (I) are useful as a medicine especially in a method of treating patients suffering from hyperlipidemia, obesity, atherosclerosis or type II diabetes. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylo-micronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, e.g. ischaemic heart disease, peripheral vascular disease, and cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthetized by the intestine, is necessary for the assembly of chylomicrons and therefore has an obligatory role in the intestinal absorption of dietary fats. The present invention provides biphenylcarboxamide compounds which are acting as selective MTP inhibitors at the level of the gut wall.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

The compounds of formula (I) may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such "HMG-CoA reductase inhibitors" are, e.g., lovastatin, simvastatin, fluvastatin, pravastatin, rivastatin, and atorvastatin.

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase Any HMG-CoA reductase gene expression inhibitor may be used as the second compound in the combination therapy aspect of this invention. These agents may be HMG-CoA reductase trancription inhibitors that block the transcription of DNA or translation inhibitors that prevent translation of mRNA coding for HMG-CoA reductase into protein. Such inhibitors may either affect trancription or translation directly or may be biotransformed into compounds having the above-mentioned attributes by one or more enzymes in the cholesterol biosynthetic cascade or may lead to accumulation of a metabolite having the above-mentioned activities.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase.

Those of skill in the treatment of hyperlipidemia will easily determine the therapeutically effective amount of a compound of formula (I) from the test results presented hereinafter. In general it is contemplated that a therapeutically effective dose will be from about 0.001 mg/kg to about 5 mg/kg of body weight, more preferably from about 0.01 mg/kg to about 0.5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the biphenylcarboxamide compounds of the instant invention. The effective daily amount ranges mentioned hereinabove are therefore only guidelines.

EXPERIMENTAL PART

In the procedures described hereinafter the following abbreviations were used: "PS-DIEA" which stands for N,N-(diisopropyl)aminomethylpolystyrene resin was obtained from Argonaut (New Road, Hengoed, Mid Glamorgan CF82 8AU, United Kingdom) with product code 800279. "PS-DCC" is a N-cyclohexcylcarbodiimide N'-methyl polystyrene resin which was obtained from Calbiochem-Novabiochem AG, (Weidenmattweg 4, CH-4448 Liiufelfingen, Switzerland) with product code Novabiochem 01-64-0211. 'THF' stands for tetrahydrofuran.

A. Synthesis of the Intermediates

Example A.1 a) Preparation of

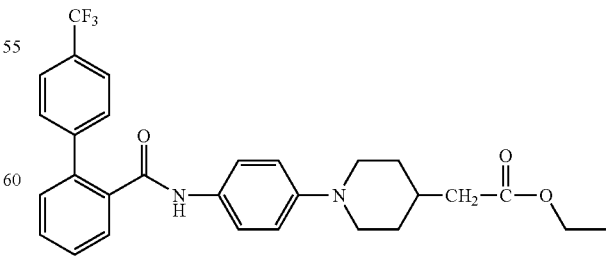

intermediate (1)

4'-(Trifluoromethyl)-[1,1'-biphenyl]-2-carboxylic acid (0.0069 mol) was dissolved in dichloromethane (400 ml) together with oxalyl chloride (0.069 mol) and dimethyl-formamide (one drop) at 0° C. Further 4'-(trifluoromethyl)-[1,1'-biphenyl]-2-carboxylic acid (0.0621 mol) was added portionwise under a stream of nitrogen. Oxalyl chloride (0.069 mol) and dimethylformamide (one drop) were added and the reaction mixture was stirred for 2 hours at 0° C. The reaction mixture was filtered, the residue was dissolved in dichloromethane (100 ml) and the resulting mixture was added dropwise at 0° C. to a mixture of 1-(4-aminophenyl)-4-piperidineacetic acid ethyl ester (0.069 mol) in triethylamine (17.5 ml) and dichloromethane (300 ml). The reaction mixture was allowed to reach room temperature in 90 minutes. The resulting reaction mixture was washed with water, dried, and the solvent was evaporated. The residue was stirred in a hot mixture of hexane and ethyl acetate and the resulting precipitate was filtered off hot over celite. The filtrate was cooled and the resulting precipitate was filtered off, washed with ether and dried, yielding 31 g of intermediate (1) (mp. 160-162° C.).

b) Preparation of intermediate (2)

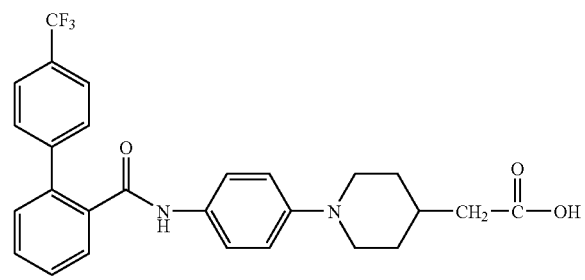

A mixture of intermediate (1) (0.015 mol) in a concentrated HCl solution (50 ml) was stirred and refluxed for 90 minutes. The resulting precipitate was filtered off, washed with water and dried. The precipitate (0.008 mol) was dissolved in a mixture of a NaOH solution (1 N, 50 ml) and 2-propanol (100 ml) and stirred for 1 hour at 50° C. The reaction mixture was cooled to room temperature and HCl (1 N, 70 ml) was added and the mixture was extracted twice with dichloromethane. The extracts were combined, evaporated and the resulting residue was triturated under dichloromethane, yielding 4.1 g of intermediate (2).

Example A.2 a) Preparation of intermediate (3)

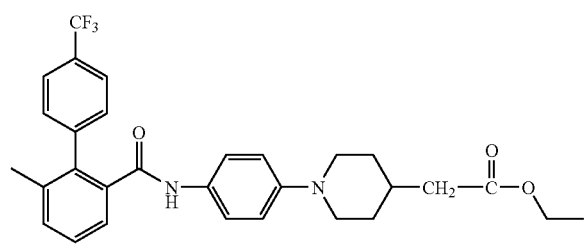

6-Methyl-4'-(trifluoromethyl)-[1,1'-biphenyl]-2-carboxylic acid (0.0025 mol) was dissolved in dry dichloromethane (140 ml) along with ethanedioyl dichloride (2.4 ml) and a few drops of dimethylformamide, at 0° C. Then, all remaining 6-methyl-4'-(trifluoromethyl)-[1,1'-biphenyl]-2-carboxylic acid (0.0225 mol) was added in portions, under a stream of nitrogen. The reaction mixture was heated gently to 40° C. until an homogeneous solution resulted and gas evolution had stopped. The mixture was allowed to cool to room temperature, then filtered off over a Buchner filter. The filter residue was dissolved in dichloromethane, then added dropwise at 0° C. to a solution of 1-(4-aminophenyl)-4-piperidineacetic acid, ethyl ester (1 equiv, 0.025 mol) and triethylamine (3 g) in dry dichloromethane (140 ml). The reaction mixture was allowed to warm to room temperature over 90 minutes. The precipitate was filtered off and dried, yielding 13.65 g of intermediate (3) (mp. 150-151° C.).

b) Preparation of intermediate (4)

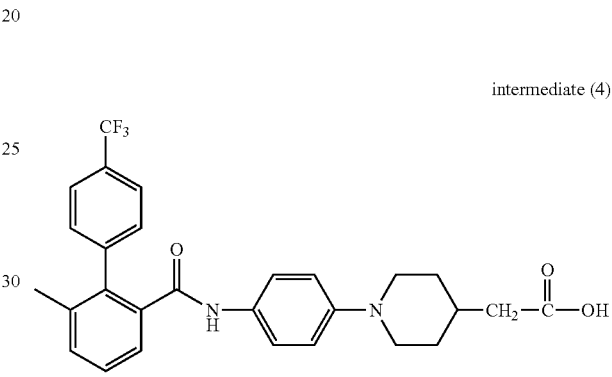

Sodium hydroxide (1 N, 100 ml) was added to a solution of intermediate (3) (0.0334 mol) in methanol (300 ml), then the reaction mixture was stirred for 2 hours at 50° C. and for 20 hours at room temperature. Water (300 ml) was added and the mixture was acidified with 1N HCl. Dichloromethane (200 ml) was added and the reaction mixture was stirred for 2 hours, then the resulting precipitate was filtered off, washed with water and with dichloromethane and finally dried, yielding 17.1 g of intermediate (4), isolated as a 1:1 hydrochloric acid salt.

Example A.3 a) Preparation of intermediate (5)

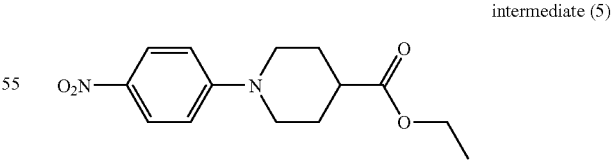

A mixture of 4-piperidinecarboxylic acid ethyl ester (0.03 mol), 1-fluoro-4-nitro-benzene (0.03 mol) and potassium carbonate (4.5 g) in dimethylformamide (50 ml) was reacted for 4 hours at 60° C., then the solvent was evaporated under reduced pressure and the obtained residue was stirred in water. The obtained yellow solid was filtered off and taken up in dichloromethane (100 ml). The organic layer was dried and the solvent was evaporated. The resulting oil was crystallised from hexane and the desired product was collected, yielding 7 g of intermediate (5) (m.p. 70-71° C.).

b) Preparation of

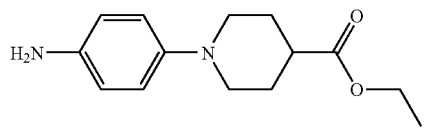

intermediate (6)

A mixture of intermediate (5) (0.025 mol) in ethanol (150 ml) was hydrogenated under pressure (30 bar=3.10$^6$ Pa)) overnight at 25° C. with Pd/C 10% (0.5 g) as a catalyst. After uptake of hydrogen (3 equivalents), the reaction mixture was filtered off and the solvent was evaporated under reduced pressure, yielding 6 g of intermediate (6).

c) Preparation of

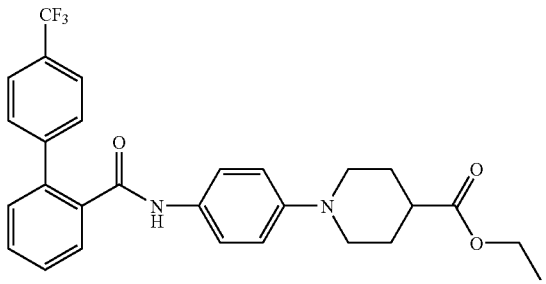

intermediate (7)

Reaction under nitrogen: 0.2 g of 4'-(trifluoromethyl)-[1,1'-biphenyl]-2-carboxylic acid in dichloromethane (50 ml) was reacted with ethanedioyl dichloride (0.01 mol) at 0° C. and then the reaction was initiated with dimethylformamide (1 drop). The remaining of 4'-(trifluoromethyl)-[1,1'-biphenyl]-2-carboxylic acid (1.8 g) was added portionwise and an extra amount of ethanedioyl dichloride was added. The reaction mixture was stirred for 2 hours at 0° C. (no acid present when sample of reaction mixture was taken up in methanol for TLC-analyses) and dichloromethane and the excess of ethanedioyl dichloride was evaporated under reduced pressure. The obtained residue was taken up in dichloromethane (50 ml) and added dropwise to a mixture of intermediate (6) (0.0075 mol) and triethylamine (0.0075 mol) in dichloromethane (50 ml) at 0° C. The resulting mixture was stirred for 1 hour at room temperature, then the organic layer was washed with water, dried and the solvent was evaporated under reduced pressure. The obtained residue was crystallised from methanol and the desired product was collected, yielding 2.9 g of intermediate (7) (mp. 190-192° C.).

d) Preparation of

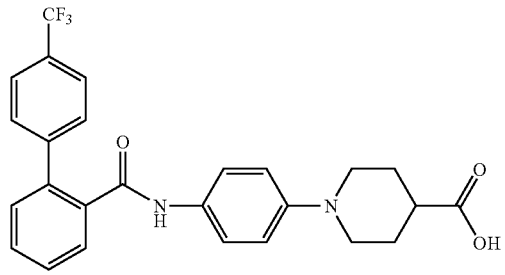

intermediate (8)

Intermediate (7) (0.006 mol) was added to a solution of NaOH (0.018 mol) in ethanol (20 ml) and water (20 ml) and then the reaction mixture was warmed to 60° C. The resulting solution was kept at 60° C. for 1 hour and was cooled. The mixture was acidified with 4N HCl and stirred for 1 hour, then the resulting precipitate was filtered off and washed with water, yielding 2.7 g of intermediate (8) (mp. 260-262° C.).

Example A.4 a) Preparation of

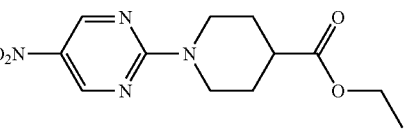

intermediate (9)

A mixture of nitromalonaldehyde sodium salt hydrate (CAS 53821-72-0) (0.06 mol), carbamimidothioic acid, methyl ester, sulfate (2:1) (0.03 mol) and 4-piperidine-carboxylic acid ethyl ester (0.047 mol) in water (200 ml) was stirred for 2 hours at 80° C. or until the methanethiol-gas evolution stopped, then the resulting precipitate was filtered off and washed with water. The solids were stirred in a minimum amount of methanol, then filtered off again and washed with ether, yielding 4.8 g of intermediate (9) (mp. 114-116° C.).

b) Preparation of

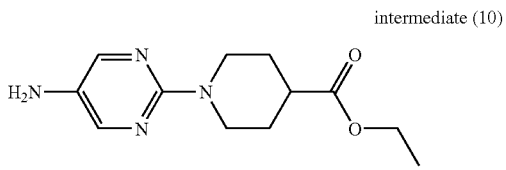 [SMILES: CCOC(=O)C1CCN(c2ncc(N)cn2)CC1]

intermediate (10)

A mixture of intermediate (9) (0.017 mol) in ethanol (100 ml) was hydrogenated for 4 hours at 60° C. with palladium-on-carbon 10% (0.5 g) as a catalyst. After uptake of hydrogen (3 equivalents), the reaction mixture was filtered off and the solvent was evaporated. The obtained residue was purified by column chromatography (eluent: ethyl acetate/hexane 1/2).

The product fractions were collected and the solvent was evaporated, yielding 3 g of intermediate (10).

c) Preparation of

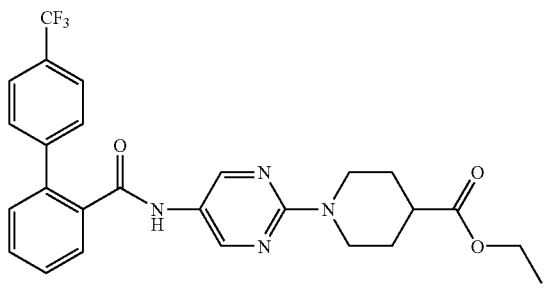

intermediate (11)

Reaction under nitrogen: 0.3 g of 4'-(trifluoromethyl)-[1,1'-biphenyl]-2-carboxylic acid in dichloromethane (50 ml) was reacted with ethanedioyl dichloride (0.01 mol) at 0° C. and then the reaction was initiated with dimethylformamide (1 drop). The remaining of 4'-(trifluoromethyl)-[1,1'-biphenyl]-2-carboxylic acid (2.7 g) was added portionwise (no acid present when reaction mixture was taken up in methanol for TLC-analyses) and the solvent was evaporated under reduced pressure. The obtained residue was taken up in dichloromethane (50 ml) and added dropwise to a mixture of intermediate (10) (0.011 mol) and triethylamine (0.011 mol) in dichloromethane (50 ml) at 0° C. The resulting mixture was stirred for 30 minutes and was further purified by column chromatography over silica gel (eluent: ethyl acetate/hexane 1/4, 1/2). The product fractions were collected and the solvent was evaporated, yielding 2.9 g of intermediate (11) (mp. 171-173° C.).

d) Preparation of

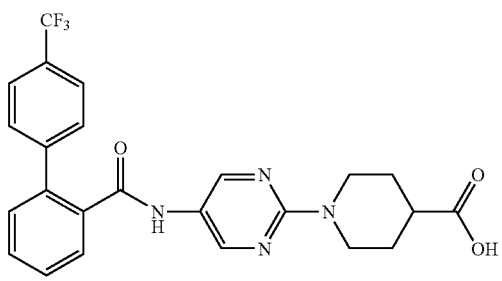

intermediate (12)

Intermediate (11) (0.006 mol) was added to a solution of NaOH (0.018 mol) in ethanol (20 ml) and water (20 ml), then the reaction mixture was heated for 1 hour at 60° C., cooled and acidified with 4N HCl. The resulting precipitate was filtered off, washed with water and dried, yielding 2.6 g of intermediate (12) (mp. 231-233° C.).

Example A.5 a) Preparation of

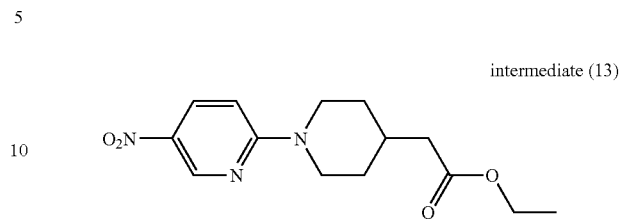

intermediate (13)

A mixture of 2-chloro-5-nitro-pyridine (0.0227 mol), 4-piperidineacetic acid, ethyl ester (0.0227 mol) and sodium carbonate (0.091 mol) in dimethylsulfoxide (40 ml) was heated at 60° C. and stirred for 2 hours, then the reaction mixture was cooled to room temperature and poured out into ice-water. The resulting precipitate was filtered off and washed with water. The crude solid was purified by crystallisation from ethyl acetate/hexane and the resulting precipitate was collected, yielding 3.2 g of intermediate (13) (mp. 99-101° C.).

b) Preparation of

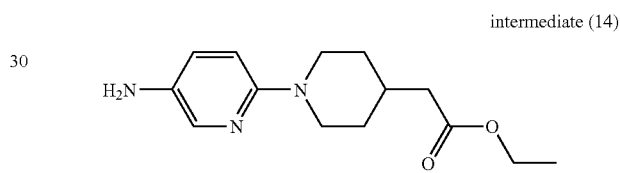

intermediate (14)

A mixture of intermediate (13) (0.0102 mol) in THF (50 ml) was hydrogenated for 30 minutes at 50° C. with palladium-on-carbon 10% (0.3 g) as a catalyst. After uptake of hydrogen (3 equivalents), the reaction mixture was cooled and the catalyst was filtered off, then the filtrate was evaporated, yielding 2.6 g of intermediate (14).

c) Preparation of

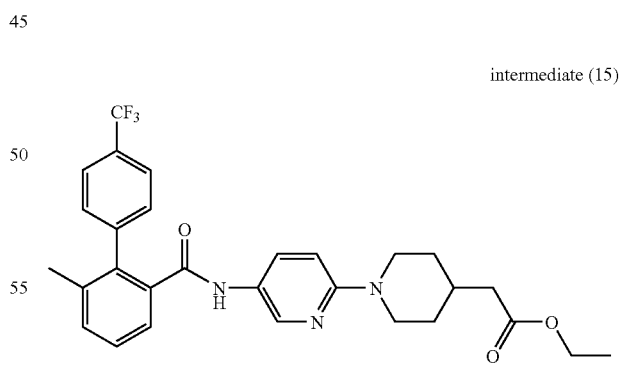

intermediate (15)

A solution of 6-methyl-4'-(trifluoromethyl)-[1,1'-biphenyl]-2-carboxylic acid (0.005 mol) in 1,4-dioxane (5 ml) was added to a solution of intermediate (14) (0.005 mol) and triethylamine (0.005 mol) in 1,4-dioxane (15 ml) at 10° C., then the reaction mixture was stirred at room temperature for 60 hours. The mixture was diluted with water and extracted with ethyl acetate (100 ml). The product was washed with brine, dried and the solvent was evaporated. The residue was purified by column chromatography (eluent: ethyl acetate/hexane 1/4). The product fractions were collected and the solvent was evaporated, yielding 1.7 g of intermediate (15) (mp. 134-137° C.).

d) Preparation of intermediate (16)

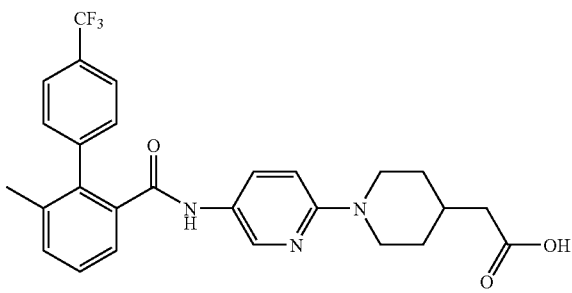

A solution of NaOH (0.0114 mol) in water (20 ml) was added to a mixture of intermediate (15) (0.0038 mol) in ethanol (20 ml) and then the reaction mixture was stirred for 2 hours at 60° C. After cooling to room temperature, the mixture was acidified with conc. HCl and the solvent was evaporated. The obtained residue was stirred in diethyl ether and the desired product was collected, yielding 2.2 g of intermediate (16).

Example A.6 a) Preparation of intermediate (17)

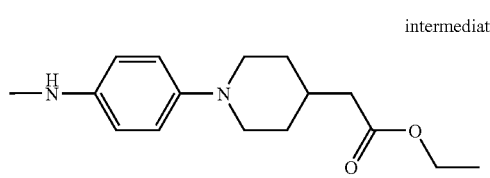

Aqueous formaldehyde 37% solution (0.0072 mol) and palladium-on-carbon (10%, 0.15 g) were added to a solution of 1-(4-aminophenyl)-4-piperidineacetic acid, ethyl ester (0.0057 mol) in ethyl acetate (40 ml) and then the reaction mixture was hydrogenated for 5 hours. After uptake of hydrogen (1 equivalent), the catalyst was filtered over celite and the celite was washed with ethyl acetate (40 ml). The filtrate was evaporated and the obtained residue was combined with the residue analogously obtained. The resulting residue was purified by Flash column chromatography (eluent: ethyl acetate/hexane 30/70). The product fractions were collected, then the solvent was evaporated and the obtained residual oil was dried, yielding 1.6 g of intermediate (17).

b) Preparation of intermediate (18)

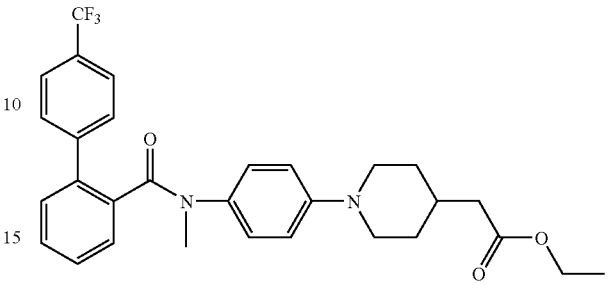

A mixture of 4'-(trifluoromethyl)-[1,1'-biphenyl]-2-carboxylic acid (0.0058 mol) in dichloromethane (40 ml) was stirred at 0° C. and under nitrogen, then ethanedioyl dichloride (0.0087 mol) was added, followed by dimethylformamide (2 drops). The resulting mixture was warmed to 15° C. for 1 hour and then to 30-35° C. for 1 hour. The solvent was evaporated and the obtained yellow solid was dissolved in dichloro-methane. This solution was added to a solution of intermediate (17) (0.0058 mol) and triethylamine (0.0087 mol) in dichloromethane under nitrogen and then the reaction mixture was stirred for 16 hours at room temperature. The mixture was diluted with ethyl acetate (100 ml) and washed with 1N HCl (50 ml), with a saturated NaHCO$_3$ solution (50 ml) and with brine (50 ml). The organic layer was dried and the solvent was evaporated. The obtained oil was further purified by flash column chromatography (eluent: ethyl acetate/hexane 30/70). The product fractions were collected and the solvent was evaporated, yielding 1.6 g of intermediate (18).

c) Preparation of intermediate (19)

Reaction performed under nitrogen: intermediate (18) (0.0029 mol) was dissolved in ethanol (20 ml) at 20° C. and then a mixture of NaOH (0.0087 mol) in water (20 ml) was added. The resulting emulsion was stirred for 16 hours at 20° C. and for 1 hour at 60° C. The reaction mixture was neutralised with 2N HCl and a suspension was formed. Ethanol was evaporated, then the aqueous concentrate was cooled to 0° C. and the resulting solids were filtered off. Dichloromethane was added to the previously obtained filtrate and then the emulsion was separated into its layers. Finally, the solvent was evaporated, yielding 1 g of intermediate (19).

Example A.7 a) Preparation of

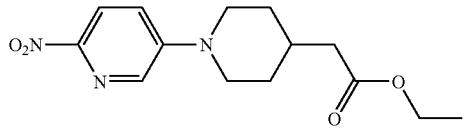
intermediate (20)

A mixture of 4-piperidineacetic acid, ethyl ester, hydrochloride (0.025 mol), 5-bromo-2-nitro-pyridine (0.03 mol) and potassium carbonate (0.06 mol) in dimethylformamide (100 ml) was heated for two days at 60° C. and then the solvent was evaporated under reduced pressure. The obtained residue was stirred in water and filtered. The filter residue was taken up in dichloromethane (100 ml), dried and the solvent was evaporated. The residue was purified by flash column chromatography over silica gel (eluent: ethyl acetate/hexane 1/5, 1/3). The product fractions were collected and the solvent was evaporated, yielding 3.3 g of intermediate (20).

b) Preparation of

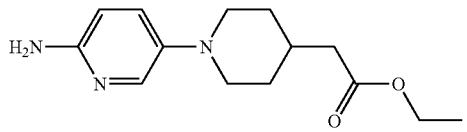
intermediate (21)

A mixture of intermediate (20) (0.01 mol) in ethanol (100 ml) was hydrogenated overnight in autoclave (30 bar=3.10⁶ Pa) at 30° C. with palladium-on-carbon (10%, 0.5 g) as a catalyst. After uptake of hydrogen (3 equivalents), the reaction mixture was filtered off and the filtrate was evaporated, yielding 2.8 g of intermediate (21).

c) Preparation of

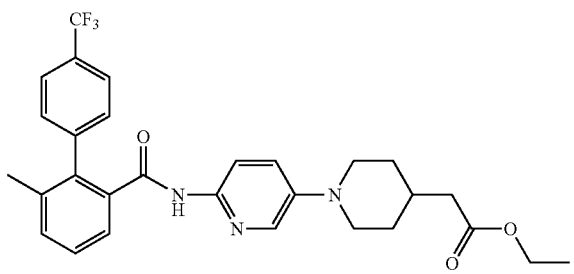
intermediate (22)

Reaction at 0° C. and under nitrogen: ethanedioyl dichloride (0.01 mol) and dimethyl-formamide (2 drops) were added to a part of 6-methyl-4'-(trifluoromethyl)-[1,1'-biphenyl]-2-carboxylic acid (0.2 g) in dichloromethane (100 ml) and then the remaining of 6-methyl-4'-(trifluoromethyl)-[1, 1'-biphenyl]-2-carboxylic acid (1.9 g) was added portionwise (no acid present when reaction mixture was taken up in methanol for TLC-analyses). The reaction mixture was stirred for 2 hours at 0° C. and the solvent was removed by evaporation. The residue was taken up in dichloromethane (25 ml) and the mixture was added dropwise to a stirring solution of intermediate (21) (0.0075 ml) and triethylamine (0.75 g) in dichloromethane (25 ml). After stirring overnight, the reaction mixture was washed with water, dried and the solvent was evaporated. The residue was purified by flash column chromatography (eluent: ethyl acetate/hexane 1/3). The product fractions were collected and the solvent was evaporated, yielding 1.5 g of intermediate (22).

d) Preparation of

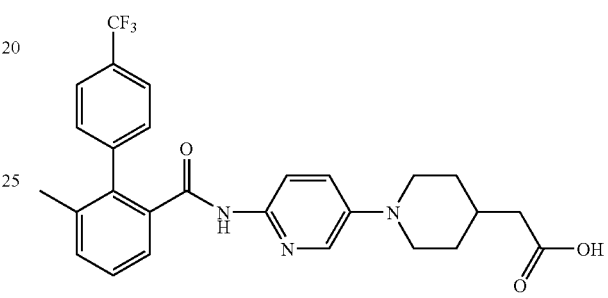
intermediate (23)

A mixture of NaOH (0.008 mol) in water (20 ml) was added to a mixture of intermediate (22) (0.003 mol) in ethanol (20 ml) and then the reaction mixture was stirred for 2 hours at 50° C. After cooling, the mixture was acidified with concentrated HCl, filtered and washed with water. The filter residue was taken up in diethyl ether, dried and the solvent was evaporated, yielding 1 g of intermediate (23).

Example A.8

Preparation of

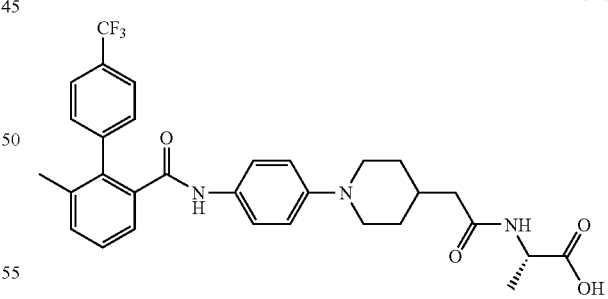
intermediate (24)

Water (28 ml) and lithium hydroxide (0.7 g) were added to a solution of compound (46) (0.013 mol) in THF (84 ml) and the reaction mixture was stirred at room temperature until the reaction was completed. The mixture was filtered and then the almost dry filter residue was taken up in a small amount of water. The resulting mixture was washed with dichloromethane and the aqueous layer was acidified carefully to a pH of 7. The resulting precipitate was filtered off and dried in a desiccator, yielding 6.9 g of intermediate (24) (mp. 170-172° C.).

Example A.9 a) Preparation of

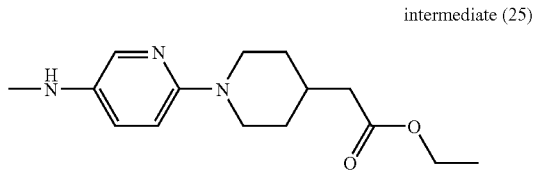 [SMILES: CCOC(=O)CC1CCN(c2ccc(NC)cn2)CC1]

intermediate (25)

A mixture of intermediate (14) (0.008 mol), aqueous formaldehyde solution (37%, 0.01 mol) and platinum-on-carbon (5%, 0.1 g) in ethyl acetate (100 ml) was stirred under hydrogen for 2 hours and then an extra portion of aqueous formaldehyde solution (37%, 0.01 mol) was added. The reaction mixture was stirred for 24 hours and was then heated overnight at 40° C. The filtrate was evaporated and the obtained residue was purified by column chromatography over silica gel (eluent: ethyl acetate/hexane 1/1). The product fractions were collected and the solvent was evaporated, yielding 1.7 g of intermediate (25).

b) Preparation of

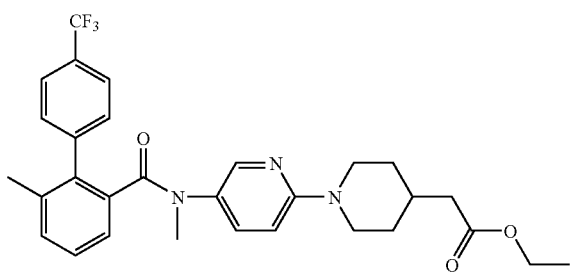

intermediate (26)

Reaction at 0° C. and under nitrogen: 0.18 g of 6-methyl-4'-(trifluoromethyl)-[1,1'-biphenyl]-2-carboxylic acid was stirred in dichloromethane (50 ml) with ethanedioyl dichloride (0.008 mol) and then the mixture was initiated with dimethylformamide (1 drop). The remaining of 6-methyl-4'-(trifluoromethyl)-[1,1'-biphenyl]-2-carboxylic acid (1.62 g) was added portionwise and the resulting mixture was stirred for 2 hours. Dichloromethane was evaporated under reduced pressure, to give Residue (I). A mixture of intermediate (25) (0.0065 mol) and triethylamine in dichloromethane (50 ml) was cooled under nitrogen to 0° C. and a solution of Residue (I) in dichloromethane (20 ml) was added dropwise. The reaction mixture was stirred for 3 hours at room temperature and was diluted with water. The organic layer was separated, washed with water, dried and the solvent was evaporated. The obtained residue was purified by flash column chromatography (eluent: ethyl acetate/hexane 1/3). The product fractions were collected and the solvent was evaporated, yield 1.2 g of intermediate (26).

c) Preparation of

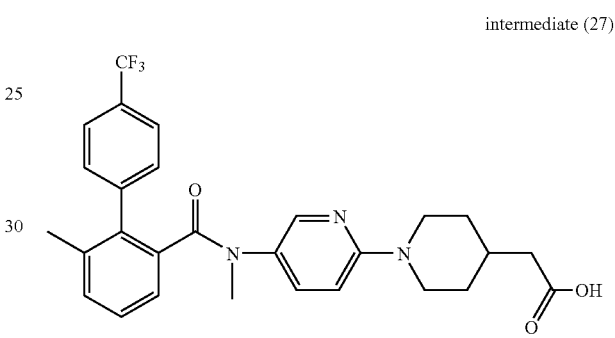

intermediate (27)

Intermediate (26) (0.0022 mol) was added to a solution of sodium hydroxide (0.0066 mol) in water (16 ml) and ethanol (30 ml) and then the reaction mixture was stirred for 18 hours at 30° C. The solvent was evaporated under reduced pressure and the obtained residue was acidified with 4N HCl. Finally, solvent was evaporated, yielding 1.2 g of intermediate (27).

Example A.10 a) Preparation of

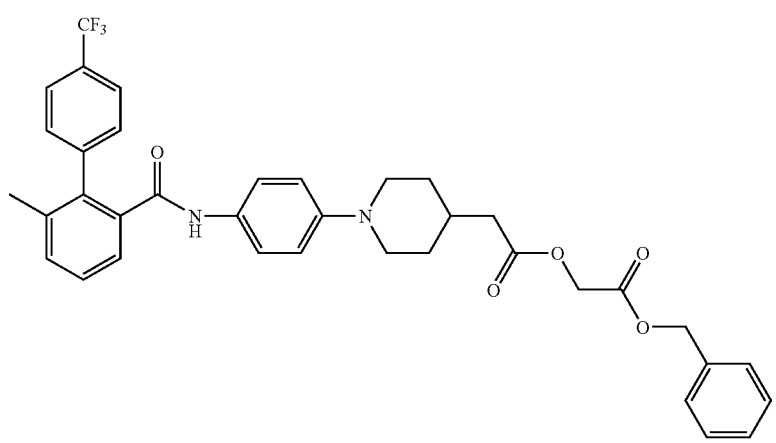

intermediate (28)

A mixture of intermediate (4) (0.0019 mol) and potassium carbonate (0.0053 mol) in dimethylformamide (30 ml) was heated for 30 minutes at 45° C., then bromo acetic acid, phenylmethyl ester (0.0029 mol) was added and the reaction mixture was heated for 3 hours at 45° C. The mixture was poured out into water (75 ml) and dichloromethane (75 ml) and stirred, then the dichloromethane layer was separated and concentrated, yielding 0.9 g of intermediate (28).

b) Preparation of intermediate (29)

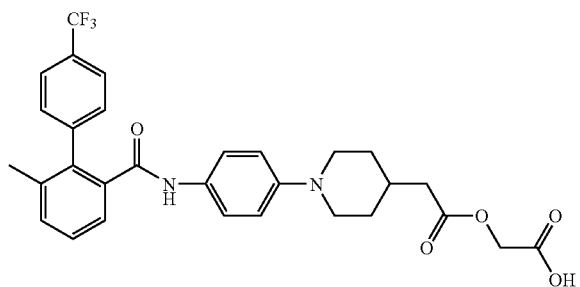

A solution of intermediate (28) (0.0014 mol) in ethyl acetate (40 ml) and ethanol (40 ml) was hydrogenated at atmospheric temperature and at room temperature for 16 hours with palladium-on-carbon (10%, 0.100 g) as a catalyst. After uptake of hydrogen (1 equivalent), the reaction mixture was filtered over celite and the filtrate was evaporated, yielding 0.600 g of intermediate (29).

B. Preparation of the Final Compounds

Example B.1

Intermediate (2) (0.0001 mol) was dissolved in dichloromethane (2 ml) and PS-DIEA (0.03 g) was added. The resulting suspension was shaken overnight at room temperature and filtered. PS-DCC (0.08 g) was added to the filtrate of the previous step and 2-(ethoxycarbonyl)piperidine (0.0001 mol) dissolved in dimethylformamide (2 ml) was added. The reaction mixture was stirred for 20 hours at room temperature and filtered. The filtrate was evaporated and purified by reverse-phase HPLC, yielding 0.001 g of compound (1).

Example B.2

N'-(ethylcarbonimidoyl)-N,N-dimethyl-1,3-propanediamine, monohydrochloride (0.0015 mol) was added to a mixture of intermediate (8) (0.001 mol), 1-hydroxy-1H-benzotriazole (0.0015 mol), 4-methylmorpholine (0.004 mol) and D-alanine, ethyl ester, hydrochloride (0.001 mol) in dichloromethane (50 ml) and the reaction mixture was stirred overnight under nitrogen. The mixture was washed with 1N HCl (20 ml), with a saturated NaHCO$_3$ solution (20 ml) and with brine, then dried and filtered off. The solvent was evaporated under reduced pressure and the obtained residue was stirred in hexane, yielding 0.470 g of compound (38) (mp. 213-215° C.).

Example B.3

Intermediate (4) (0.002 mol), dimethylformamide (50 ml) and N-ethyl-N-(1-methylethyl)-2-propanamine (0.5 ml) were stirred until complete dissolution, then 1-[bis(dimethylamino)methylene]-1H-benzotriazolium, hexafluorophosphate(1-), 3-oxide (0.0033 mol) was added and the mixture was stirred for 15 minutes. L-glutamic acid, diethyl ester, hydrochloride (0.003 mol) was added and the reaction mixture was stirred overnight. The mixture was poured out into water and extracted with ethyl acetate (<30° C.). The organic layer was evaporated and the obtained residue was triturated under diisopropyl ether with 3 drops of 2-propanol. The resulting precipitate was filtered off and purified by column chromatography over reverse phase silica (eluent: dichloromethane). The product fractions were collected and the solvent was evaporated, yielding 0.6 g of compound (52).

The compounds (2) to (34) were prepared by reacting intermediate (1) with one of the following reagents: 2-(R)-piperidine-carboxylic acid methyl ester hydrochloride, 2-(S)-piperidinecarboxylic acid methyl ester hydrochloride, 3-(ethoxycarbonyl)piperidine, (S)-3-piperidinecarboxylic acid ethyl ester, (R)-3-piperidinecarboxylic acid ethyl ester, ethyl D-prolinate hydrochloride, 4-trans-hydroxy-L-proline ethyl ester hydrochloride, 4-trans-hydroxy-L-proline methyl ester hydrochloride, 4-cis-hydroxy-L-proline methyl ester hydrochloride, (±)-alanine methyl ester hydrochloride, ethyl (S)-alaninate hydro-chloride, ethyl (R)-alaninate hydrochloride, (±)-valine methyl ester hydrochloride, (S)-valine ethyl ester hydrochloride, (R)-valine ethyl ester hydrochloride, (R)-phenyl-glycine ethyl ester hydrochloride, (S)-phenylglycine ethyl ester hydrochloride, (±)-phenylalanine methyl ester hydrochloride, (S)-phenylalanine ethyl ester, (R)-phenyl-alanine ethyl ester, 3-aminopropionic acid ethyl ester hydrochloride, ethyl N-methyl-lycinate hydrochloride, diethyl L-glutamate hydrochloride, (S)-2-amino-4-[[(1,1-dimethyl-ethoxy)carbonyl]amino]-butanoic acid methyl ester hydrochloride, N5-[(1,1-dimethyl-ethoxy)carbonyl]-L-ornithine methyl ester hydrochloride, N6-[(1,1-dimethyl-ethoxy)carbonyl]-L-lysine methyl ester hydrochloride, alanine ethyl ester hydro-chloride, (S)-leucine ethyl ester hydrochloride, tryptophan ethyl ester hydrochloride, S-methionine ethyl ester hydrochloride, (S)-tyrosine ethyl ester hydrochloride, (S)-proline ethyl ester hydrochloride, or 3-amino-3-benzo[1,3]dioxol-5-yl-propionic acid ethyl ester hydrochloride.

Table F-1 lists the compounds that were prepared according to the one of the above Examples.

TABLE F-1

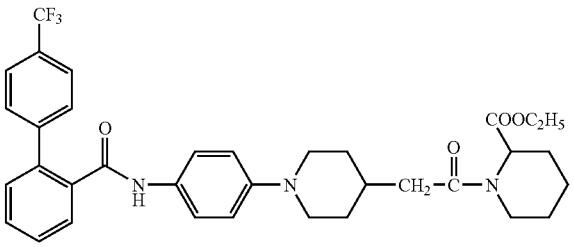

Co. No. 1; Ex. B.1

TABLE F-1-continued
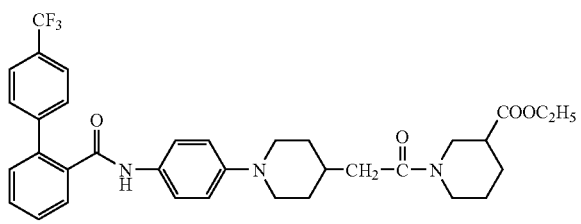
Co. No. 2; Ex. B.1
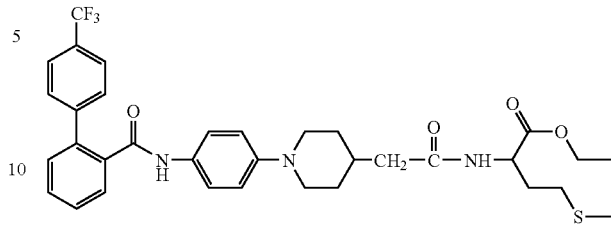
Co. No. 7; Ex. B.1
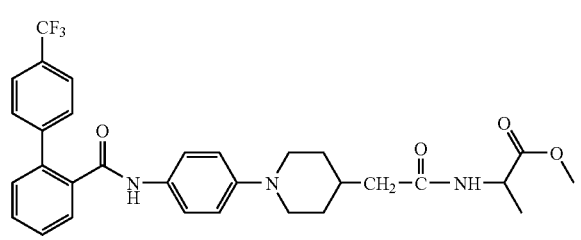
Co. No. 3; Ex. B.1
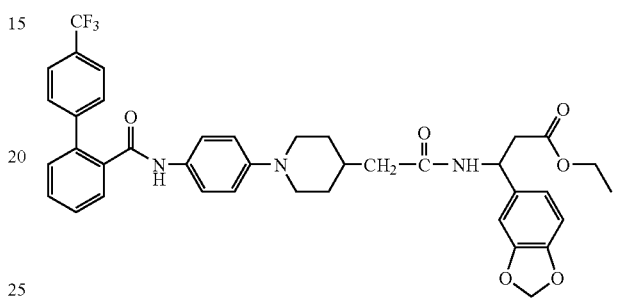
Co. No. 8; Ex. B.1
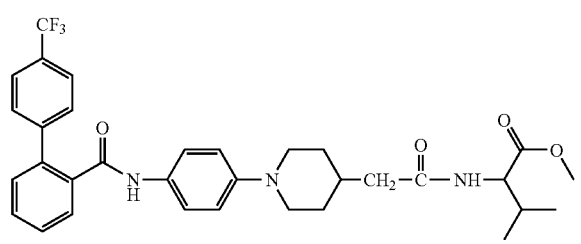
Co. No. 4; Ex. B.1
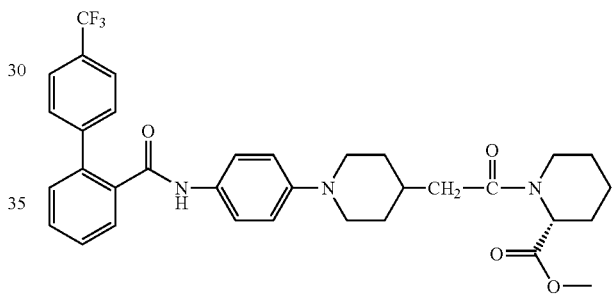
Co. No. 9; Ex. B.1; (R)
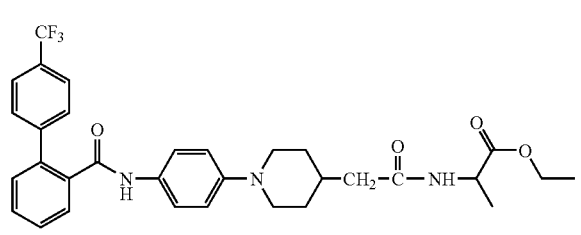
Co. No. 5; Ex. B.1
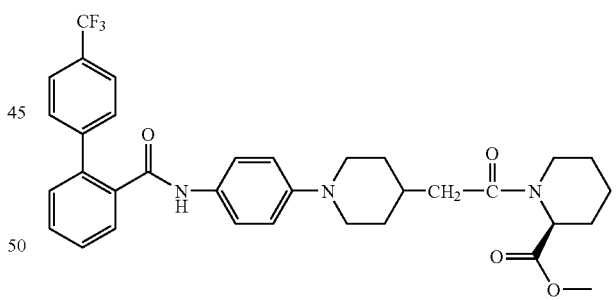
Co. No. 10; Ex. B.1; (S)
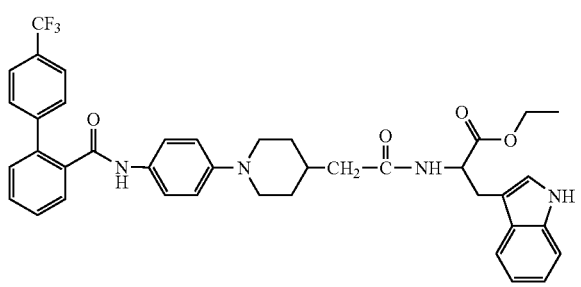
Co. No. 6; Ex. B.1
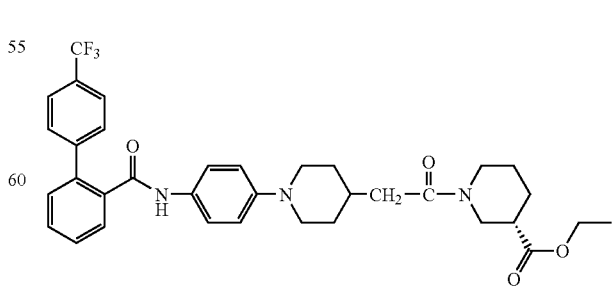
Co. No. 11; Ex. B.1; (S)

TABLE F-1-continued
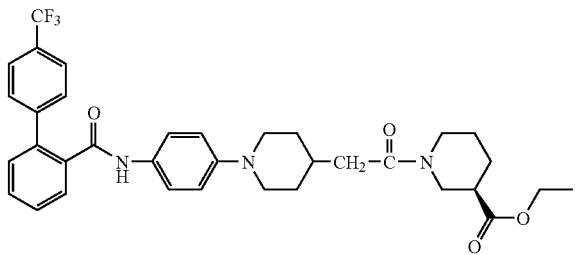
Co. No. 12; Ex. B.1; (R)
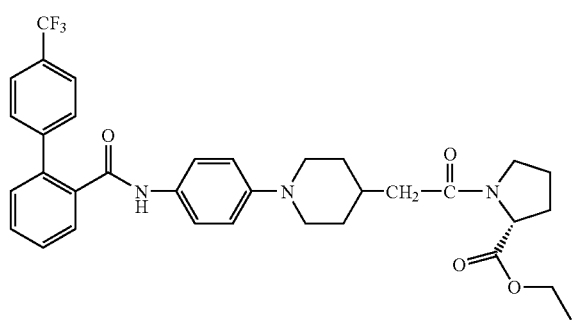
Co. No. 13; Ex. B.1; (R)
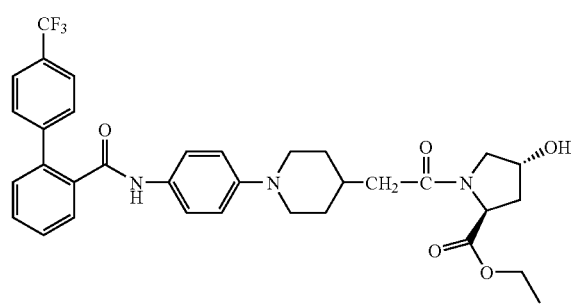
Co. No. 14; Ex. B.1; (2S-trans)
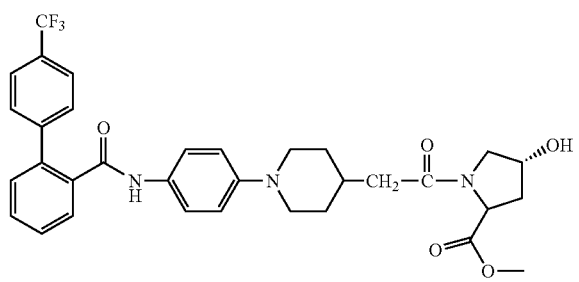
Co. No. 15; Ex. B.1; (2S-trans)
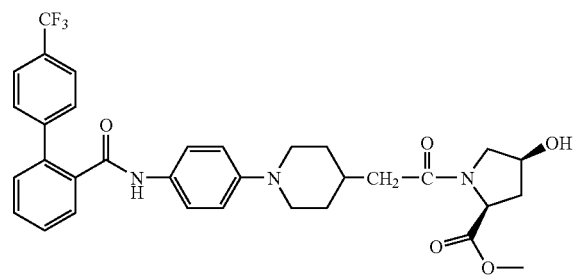
Co. No. 16; Ex. B.1; (2S-cis)
TABLE F-1-continued
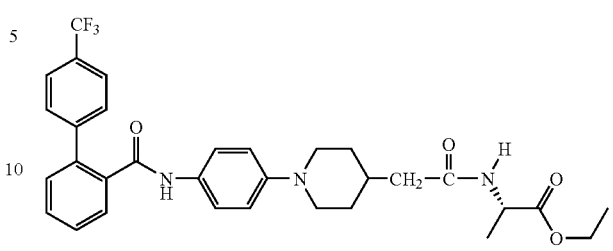
Co. No. 17; Ex. B.1; (S); $[\alpha]_D^{20} = -11.82°$ (c = 0.66 % w/v in methanol)
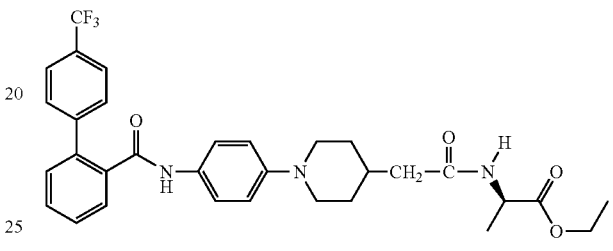
Co. No. 18; Ex. B.1; (R); $[\alpha]_D^{20} = +10.43°$ (c = 0.47 % w/v in methanol)
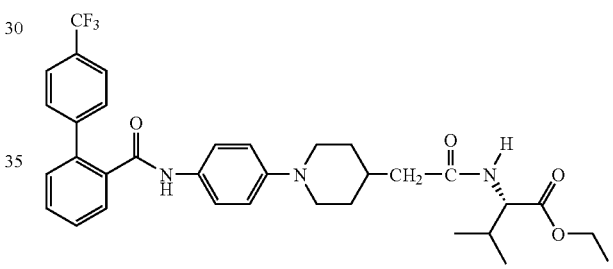
Co. No. 19; Ex. B.1; (S)
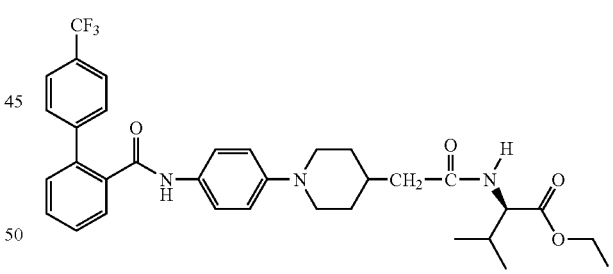
Co. No. 20; Ex. B.1; (R)
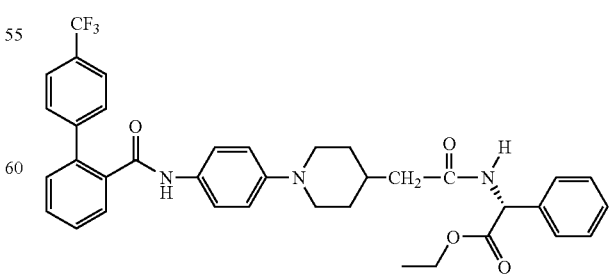
Co. No. 21; Ex. B.1; (R)

TABLE F-1-continued
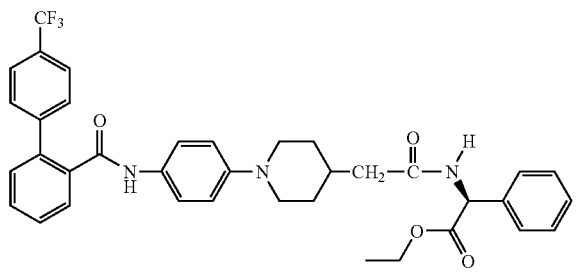
Co. No. 22; Ex. B.1; (S)
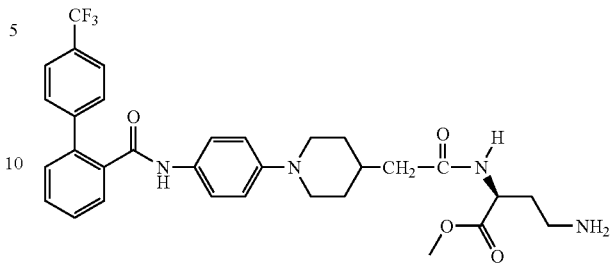
Co. No. 27; Ex. B.1; (S)
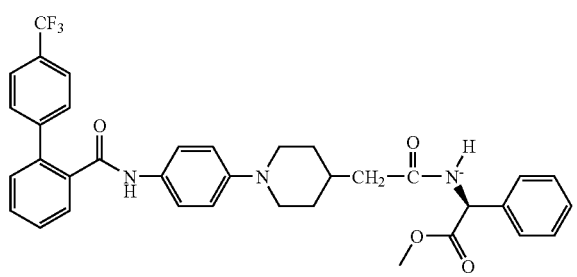
Co. No. 23; Ex. B.1; (S)
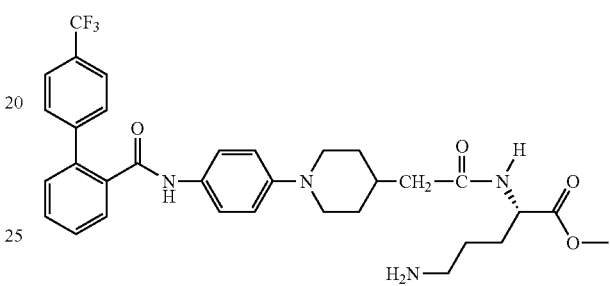
Co. No. 28; Ex. B.1; (S)
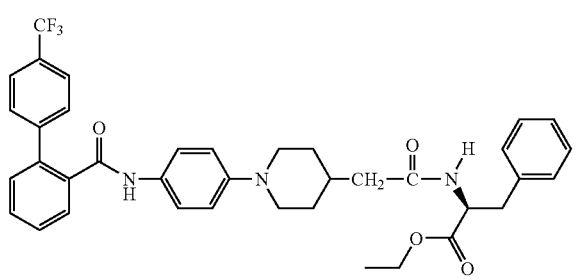
Co. No. 24; Ex. B.1; (S)
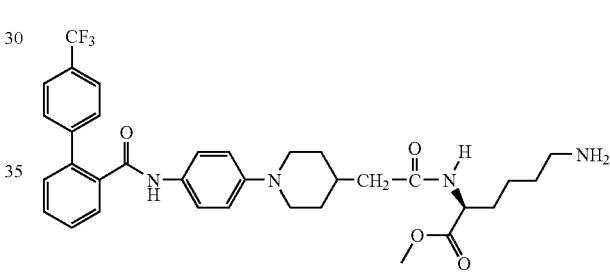
Co. No. 29; Ex. B.1; (S)
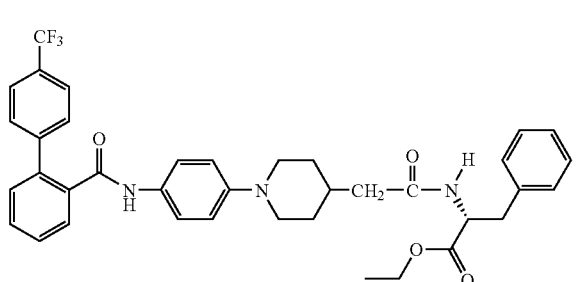
Co. No. 25; Ex. B.1; (R)
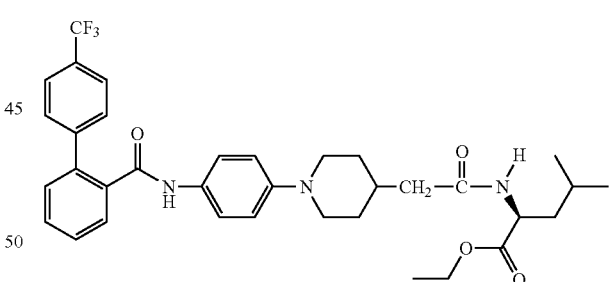
Co. No. 30; Ex. B.1; (S)
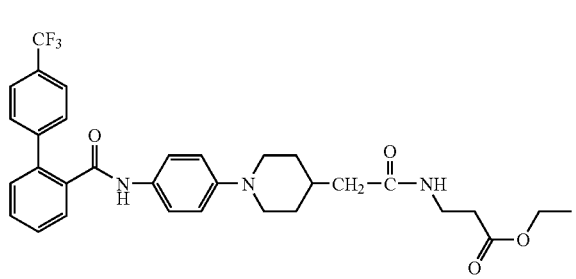
Co. No. 26; Ex. B.1;
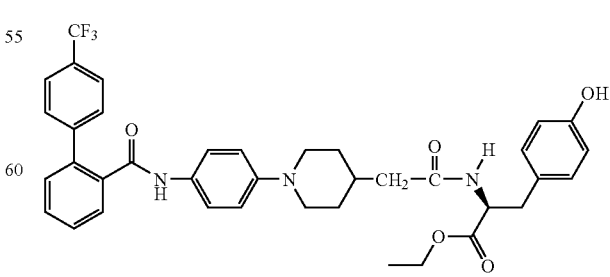
Co. No. 31; Ex. B.1; (S)

TABLE F-1-continued
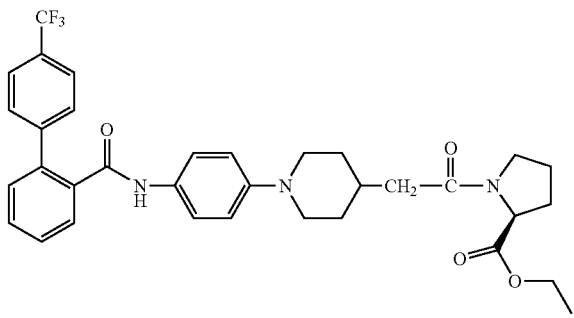
Co. No. 32; Ex. B.1; (S)
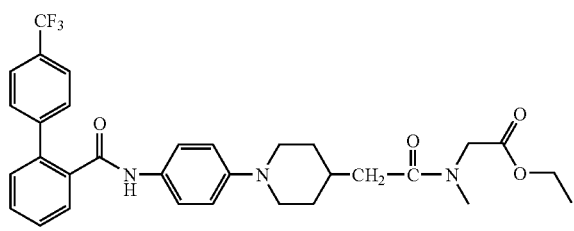
Co. No. 33; Ex. B.1
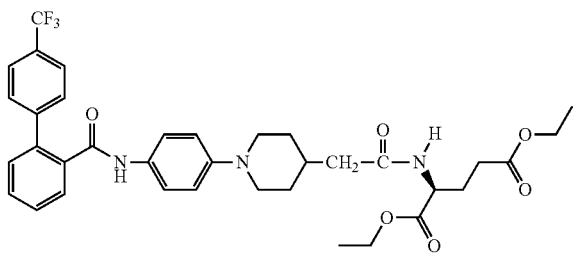
Co. No. 34; Ex. B.1; (S)
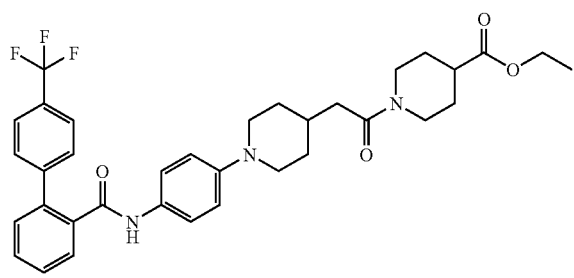
Co. No. 35; Ex. B.1
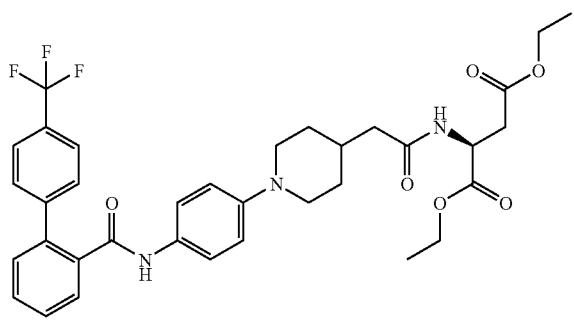
Co. No. 36; Ex. B.1; (S)
TABLE F-1-continued
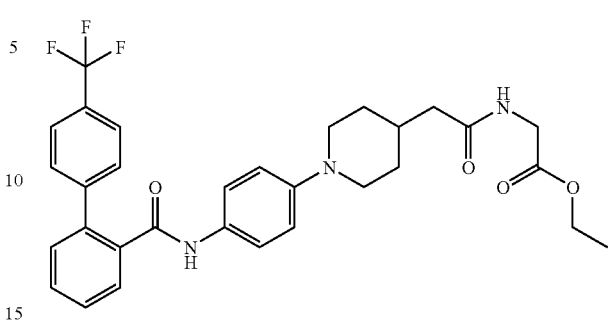
Co. No. 37; Ex. B.1
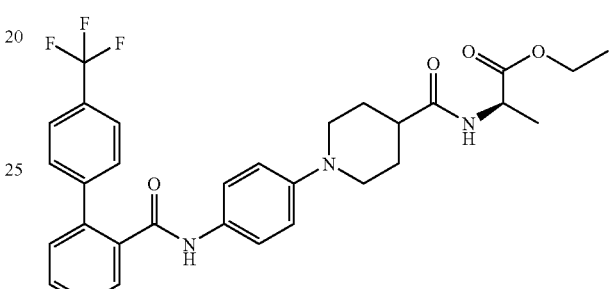
Co. No. 38; Ex. B.2; (R); mp. 213–215° C.;
$[\alpha]_D^{20} = +13°$ (c = 0.5 % w/v in ethanol)
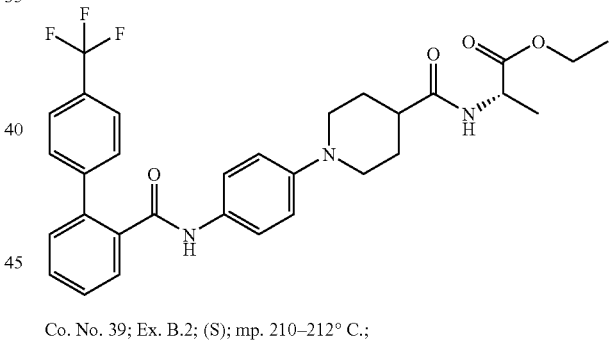
Co. No. 39; Ex. B.2; (S); mp. 210–212° C.;
$[\alpha]_D^{20} = -18°$ (c = 0.5 % w/v in ethanol)
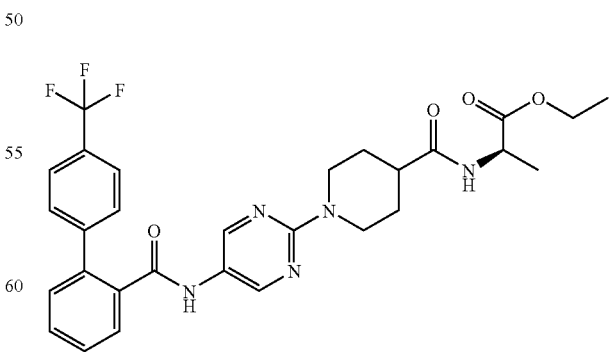
Co. No. 40; Ex. B.2; (R); mp. 200–202° C.;
$[\alpha]_D^{20} = +27°$ (c = 0.5 % w/v in ethanol)

TABLE F-1-continued
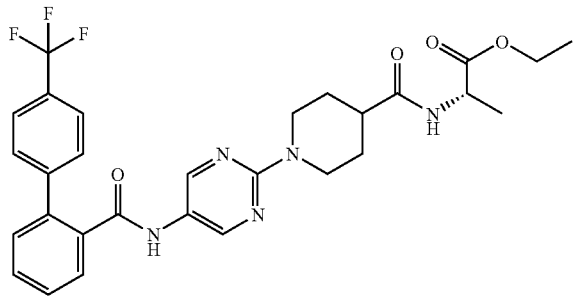
Co. No. 41; Ex. B.2; (S); mp. 203–205° C.;
[α]$_D^{20}$ = -21° (c = 0.5 % w/v in ethanol)
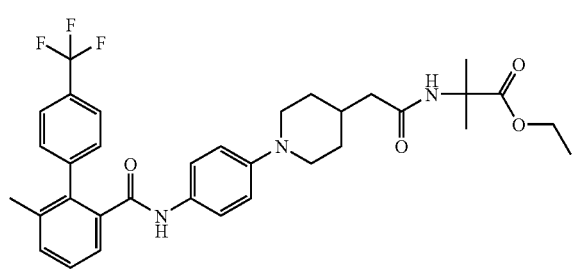
Co. No. 42; Ex. B.2; mp. 210–212° C.
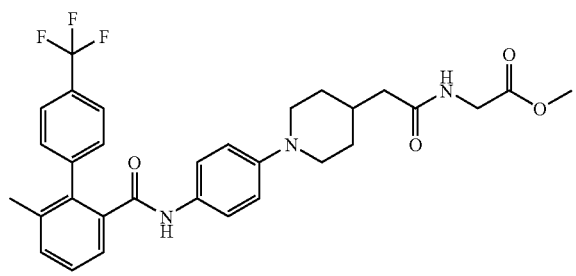
Co. No. 43; Ex. B.2; mp. 200–202° C.
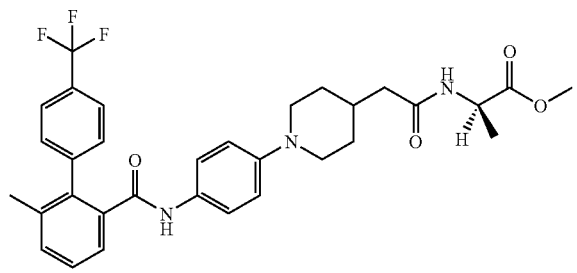
Co. No. 44; Ex. B.2; (R); mp. 188–190° C.
TABLE F-1-continued
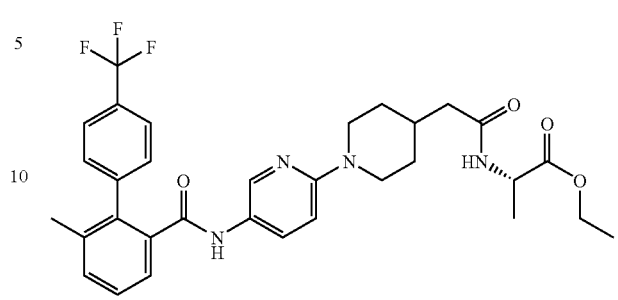
Co. No. 45; Ex. B.2; (S); [α]$_D^{20}$ = -14°
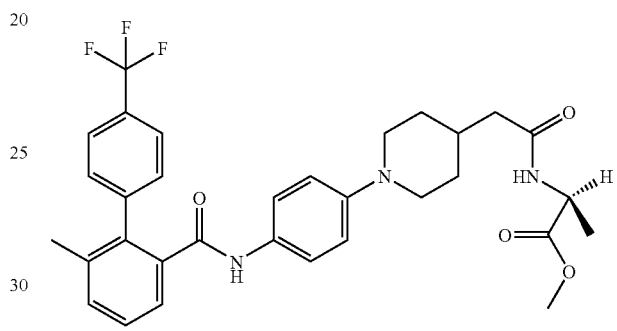
Co. No. 46; Ex. B.2; (S); mp. 190–191° C.;
[α]$_D^{20}$ = -14°
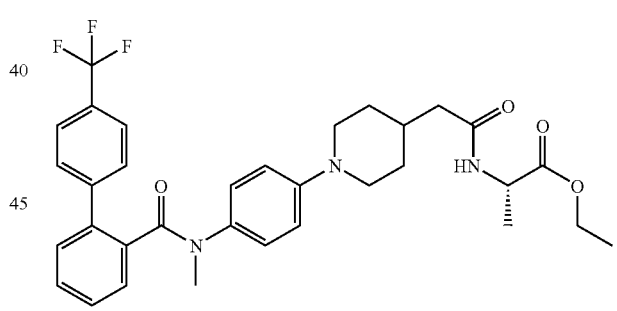
Co. No. 47; Ex. B.2; (S); mp. 58–60° C.;
[α]$_D^{20}$ = -8°
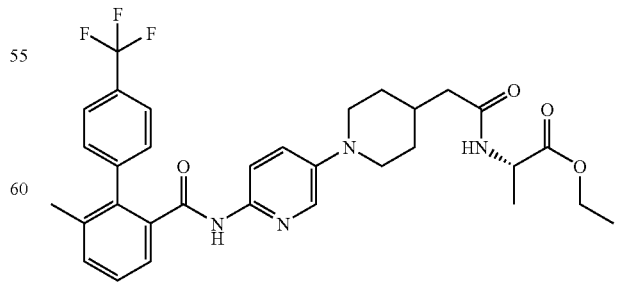
Co. No. 48; Ex. B.2; (S); [α]$_D^{20}$ = -11°

TABLE F-1-continued

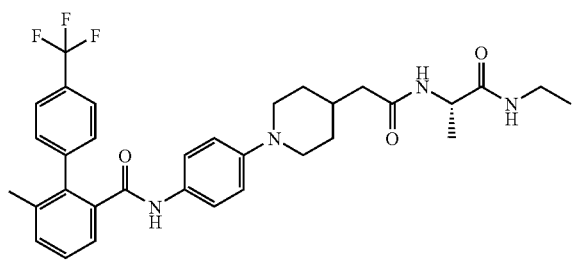

Co. No. 49; Ex. B.2; (S); mp. 158–160° C.

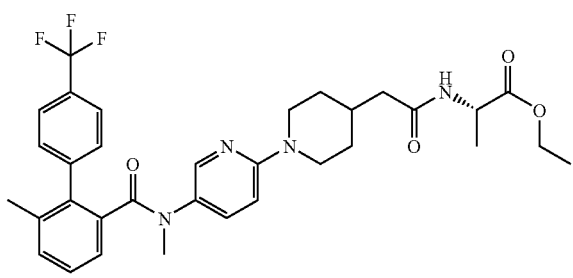

Co. No. 50; Ex. B.2; (S); $[\alpha]_D^{20}$ = -4°

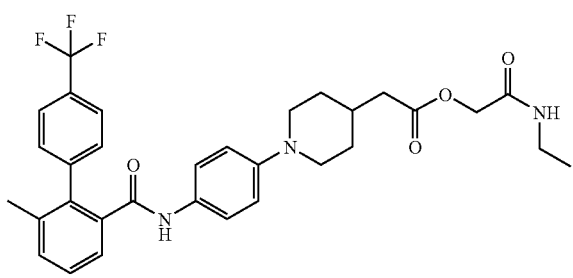

Co. No. 51; Ex. B.2; mp. 147–148° C.

Co. No. 52; Ex. B.3; (S)

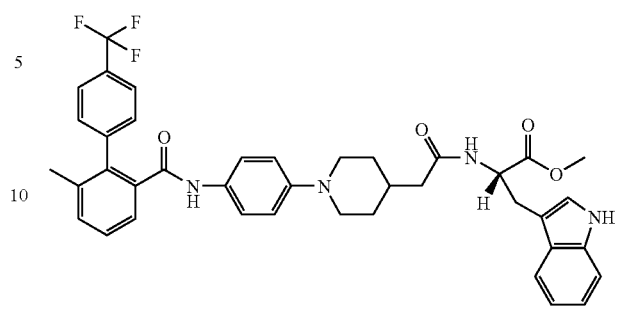

Co. No. 53; Ex. B.3; (S); $[\alpha]_D^{20}$ = -21.35°
(c = 0.2436% w/v in methanol)

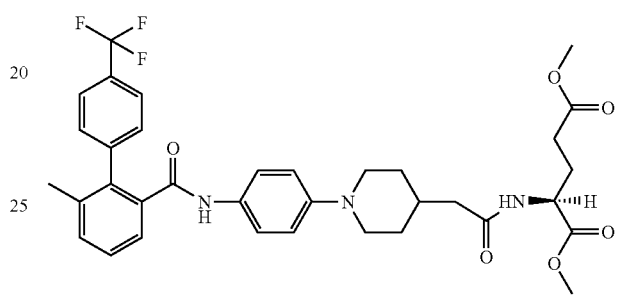

Co. No. 54; Ex. B.3; (S)

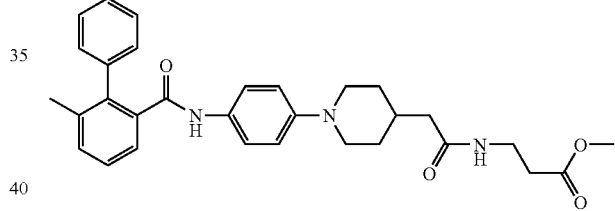

Co. No. 55; Ex. B.3

Compound Identification

The compound (8) to (34) were identified by LC/MS using a gradient elution system on a reversed phase HPLC. The compounds are identified by their specific retention time and their protonated molecular ion MH⁺ peak. The HPLC gradient was supplied by a Waters Alliance HT 2790 system with a columnheater set at 40° C. Flow from the column was split to a Waters 996 photodiode array (PDA) detector and a Waters-Micromass ZQ mass spectrometer with an electrospray ionization source operated in positive and negative ionization mode. Reversed phase HPLC was carried out on a Xterra MS C18 column (3.5 µm, 4.6×100 mm) with a flow rate of 1.6 ml/min. Three mobile phases (mobile phase A 95% 25 mM ammoniumacetate+5% acetonitrile; mobile phase B: acetonitrile; mobile phase C: methanol) were employed to run a gradient condition from 100% A to 50% B and 50% C in 10 minute, to 100% B in 1 minute, 100% B for 3 minute and reequilibrate with 100% A for 2.5 minutes. An injection volume of 10 µL was used.

Mass spectra were acquired by scanning from 100 to 1000 in 1 s using a dwell time of 0.1 s. The capillary needle voltage was 3 kV and the source temperature was maintained at 140° C. Nitrogen was used a the nebulizer gas. Cone voltage was 10 V for positive ionzation mode and 20 V for negative ionization mode. Data acquisition was performed with a Waters-Micromass MassLynx-Openlynx data system.

TABLE F-2 retention time (RT in minutes) and molecular weight as the MH+

| Co. No. | RT | MW (MH+) |
|---|---|---|
| 1 | 9.06 | 622 |
| 2 | 8.85 | 622 |
| 3 | 8.1 | 568 |
| 4 | 8.62 | 596 |
| 5 | 8.37 | 582 |
| 6 | 9.02 | 597 |
| 7 | 8.8 | 642 |
| 8 | 8.88 | 702 |
| 9 | 8.84 | 608 |
| 10 | 8.84 | 608 |
| 11 | 8.85 | 622 |
| 12 | 8.84 | 622 |
| 13 | 8.6 | 608 |
| 14 | 7.96 | 624 |
| 15 | 7.7 | 610 |
| 16 | 7.7 | 610 |
| 17 | 8.35 | 582 |
| 18 | 8.35 | 582 |
| 19 | 8.85 | 610 |
| 20 | 8.85 | 610 |
| 21 | 8.96 | 644 |
| 22 | 8.94 | 644 |
| 23 | 8.86 | 644 |
| 24 | 9.06 | 658 |
| 25 | 9.06 | 658 |
| 26 | 8.22 | 582 |
| 27 | 7.13 | 597 |
| 28 | 7.14 | 611 |
| 29 | 7.22 | 625 |
| 30 | 9.06 | 624 |
| 31 | 8.55 | 674 |
| 32 | 8.63 | 608 |
| 33 | 8.46 | 580 |
| 34 | 8.69 | 666 |
| 35 | 8.73 | 622 |
| 36 | 8.6 | 654 |
| 37 | 8.18 | 568 |

C. Pharmacological Examples

C.1. Quantification of the Secretion of ApoB

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM Mops, 40 mM NaH$_2$PO$_4$, 100 mM NaF, 0.2 mM DTT, 5 mM EDTA, 5 mM EGTA, 1% Triton-X-100, 0.5% sodium deoxycholate (DOC), 0.1% SDS, 0.2 µM leupeptin and 0.2 µM PMSF. Radioactivity in the pellet was quantified by liquid scintillation counting.

Resulting IC$_{50}$ values are enumerated in Table C.1. When the calculated IC$_{50}$ was below 6, not enough data points were available at the tested concentrations to calculate an IC$_{50}$ value.

TABLE C.1 pIC50 values (= −log IC$_{50}$ value)

| Co. No. | pIC50 |
|---|---|
| 1 | <6 |
| 2 | 7.185 |
| 3 | 7.212 |
| 4 | 7.314 |
| 5 | >7.523 |
| 6 | >7.523 |
| 7 | 6.859 |
| 8 | >7.523 |
| 9 | <6 |
| 10 | <6 |
| 11 | <6 |
| 12 | <6 |
| 13 | <6 |
| 14 | <6 |
| 15 | <6 |
| 16 | <6 |
| 17 | <6 |
| 18 | >7.523 |
| 19 | 6.937 |
| 20 | >7.523 |
| 21 | 6.919 |
| 22 | 7.261 |
| 23 | <6 |
| 24 | 6.075 |
| 25 | <6 |
| 26 | 7.232 |
| 27 | 6.192 |
| 28 | <6 |
| 29 | <6 |
| 30 | 6.24 |
| 31 | <6 |
| 32 | 6.392 |
| 33 | <6 |
| 34 | <6 |
| 35 | <6 |
| 37 | 7.349 |
| 42 | 6.819 |
| 43 | 8.153 |
| 44 | 7.675 |
| 45 | 6.017 |
| 46 | 6.661 |
| 47 | <6 |
| 48 | 6.174 |
| 49 | 7.761 |
| 51 | 7.809 |
| 52 | 7.131 |
| 53 | 6.901 |
| 54 | 6.312 |
| 55 | 8.22 |

C.2. MTP assay

MTP activity was measured using an assay similar to one described by J. R. Wetterau and D. B. Zilversmit in *Chemistry and Physics of Lipids*, 38, 205-222 (1985). To prepare the donor and acceptor vesicles, the appropriate lipids in chloroform were put into a glass test tube and dried under a stream of N$_2$. A buffer containing 15 mM Tris-HCl pH 7.5, 1 mM EDTA, 40 mM NaCl, 0.02% NaN$_3$ (assay buffer) was added to the dried lipid. The mixture was vortexed briefly and the lipids were then allowed to hydrate for 20 min on ice. Vesicles were then prepared by bath sonication (Branson 2200) at room temperature for maximum 15 min. Butylated hydroxytoluene was included in all vesicle preparations at a concentration of 0.1%. The lipid transfer assay mixture contained donor vesicles (40 nmol phosphatidylcholine, 7.5 mol % of cardiolipin and 0.25 mol % glycerol tri [1-$^{14}$C]-oleate), acceptor vesicles (240 nmol phosphatidylcholine) and 5 mg BSA in a total volume of 675 µl in a 1.5 ml microcentrifuge tube. Test compounds were added dissolved in DMSO (0.13% final concentration). After 5 minutes of pre-incubation at 37° C., the reaction was started by the addition of MTP in 100 μl dialysis buffer. The reaction was stopped by the addition of 400 μl DEAE-52 cellulose pre-equilibrated in 15 mM Tris-HCl pH 7.5, 1 mM EDTA, 0.02% $NaN_3$ (1:1, vol/vol). The mixture was agitated for 4 min and centrifuged for 2 min at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles. The percent triglyceride transfer from donor to acceptor vesicles measured results in a "% C" value (% control) of 100% when the test compound did not inhibit MTP activity and a lower % C value when the test compound did inhibit the activity of MTP.

Resulting $IC_{50}$ values are enumerated in Table C.2. When the calculated $IC_{50}$ was below 7, not enough data points were available at the tested concentrations to calculate an $IC_{50}$ value.

TABLE C.2 pIC50 values (= −log $IC_{50}$ value)

| Co. No. | pIC50 |
|---------|-------|
| 1 | <7 |
| 2 | <6 |
| 3 | 8.107 |
| 4 | 7.384 |
| 5 | 8.687 |
| 6 | 8.031 |
| 7 | 7.593 |
| 8 | 7.696 |
| 9 | <7 |
| 10 | <7 |
| 11 | <7 |
| 12 | <7 |
| 13 | <7 |
| 14 | <7 |
| 15 | <7 |
| 16 | <7 |
| 17 | 8.252 |
| 18 | 8.466 |
| 19 | <7 |
| 20 | 8.196 |
| 21 | 8.473 |
| 22 | 8.049 |
| 23 | 8.146 |
| 24 | 7.115 |
| 26 | 8.075 |
| 27 | <7 |
| 28 | <7 |
| 29 | <7 |
| 30 | 7.657 |
| 31 | 7.091 |
| 32 | 7.501 |
| 33 | 7.158 |
| 34 | 7.916 |
| 35 | <7 |
| 36 | 7.404 |
| 37 | 8.3 |
| 42 | 7.827 |
| 43 | 7.982 |
| 44 | 8.77 |
| 49 | 8.041 |
| 50 | 7.981 |
| 51 | 8.219 |
| 52 | 8.523 |
| 53 | 7.804 |
| 54 | 8.507 |
| 55 | 8.791 |

The invention claimed is:
1. A compound of formula (I)

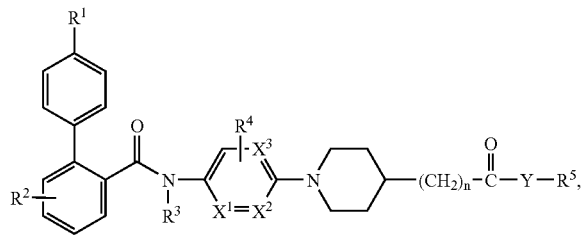

the N-oxides, the pharmaceutically acceptable acid addition salts and the stereochemically isomeric forms thereof, wherein
$R^1$ is hydrogen, $C_{1-4}$alkyl, halo, or polyhalo$C_{1-4}$alkyl;
$R^2$ is hydrogen, $C_{1-4}$alkyl, halo, or polyhalo$C_{1-4}$alkyl;
$R^3$ is hydrogen or $C_{1-4}$alkyl;
$R^4$ is hydrogen, $C_{1-4}$alkyl, or halo;
n is an integer 0, or 1;
$X^1$ is carbon and $X^2$ is carbon; or $X^1$ is nitrogen and $X^2$ is carbon;
or $X^1$ is carbon and $X^2$ is nitrogen;
$X^3$ is carbon or nitrogen;
Y represents O, or $NR^6$ wherein $R^6$ is hydrogen or $C_{1-4}$alkyl;
$R^5$ represents a radical of formula

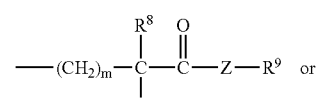

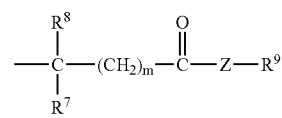

wherein
m is an integer 0, 1, or 2;
Z is O or NH;
$R^7$ is hydrogen,
$C_{1-6}$alkyl;
$C_{1-6}$alkyl substituted with hydroxy, amino, mono- or di($C_{1-4}$alkyl)amino, $C_{1-4}$alkyloxycarbonyl, aminocarbonyl, aryl or heteroaryl;
$C_{1-4}$alkyl-O—$C_{1-4}$alkyl;
$C_{1-4}$alkyl-S—$C_{1-4}$alkyl; or
aryl;
$R^8$ is hydrogen or $C_{1-6}$alkyl;
$R^9$ is $C_{1-4}$alkyl;
or when Y represents $NR^6$ the radicals $R^5$ and $R^6$ may be taken together with the nitrogen to which they are attached to form pyrrolidinyl substituted with $C_{1-4}$alkyloxycarbonyl and optionally further substituted with hydroxy; or piperidinyl substituted with $C_{1-4}$alkyloxycarbonyl;
aryl is phenyl; phenyl substituted with one, two or three substituents each independently selected from $C_{1-4}$alkyl, $C_{1-4}$alkyloxy, halo, hydroxy, nitro, cyano, C$_{1-4}$alkyloxycarbonyl, trifluoromethyl, or trifluoromethoxy; or benzo[1,3]dioxolyl; and heteroaryl is imidazolyl, thiazolyl, indolyl, or pyridinyl.

2. A compound as claimed in claim 1 wherein X$^1$, X$^2$ and X$^3$ are carbon.

3. A compound as claimed in claim 1 wherein R$^1$ is trifluoromethyl; R$^2$ is hydrogen; R$^3$ is hydrogen; R$^4$ is hydrogen; X$^1$, X$^2$ and X$^3$ are carbon; n is the integer 1; Y represents NR$^6$ wherein R$^6$ is hydrogen or methyl; and R$^5$ is a radical of formula (a-1) wherein m is the integer 0.

4. A compound as claimed in claim 1 wherein R$^1$ is trifluoromethyl; R$^2$ is hydrogen; R$^3$ is hydrogen; R$^4$ is hydrogen; X$^1$, X$^2$ and X$^3$ are carbon; n is the integer 1; Y represents NR$^6$ wherein R$^6$ is hydrogen or methyl; and R$^5$ is a radical of formula (a-1) wherein m is the integer 1.

5. A compound as claimed in claim 1 wherein R$^1$ is trifluoromethyl; R$^2$ is hydrogen; R$^3$ is hydrogen; R$^4$ is hydrogen; X$^1$, X$^2$ and X$^3$ are carbon; n is the integer 1; Y represents NR$^6$ wherein R$^6$ is hydrogen or methyl; and R$^5$ is a radical of formula (a-2) wherein m is the integer 1.

6. A compound as claimed in claim 1 wherein R$^1$ is trifluoromethyl; R$^2$ is hydrogen; R$^3$ is hydrogen; R$^4$ is hydrogen; X$^1$, X$^2$ and X$^3$ are carbon; n is the integer 1; Y represents NR$^6$ and R$^5$ and R$^6$ are taken together with the nitrogen to which they are attached to form pyrrolidinyl substituted with C$_{1-4}$alkyloxycarbonyl and optionally further substituted with hydroxy, or piperidinyl substituted with C$_{1-4}$alkyloxy-carbonyl.

7. A pharmaceutical composition comprising a pharmaceutically acceptable carrier and a therapeutically active amount of a compound as claimed in claim 1.

8. A process for preparing a pharmaceutical composition as claimed in claim 7 wherein a therapeutically active amount of a compound as claimed in claim 1 is intimately mixed with a pharmaceutically acceptable carrier.

* * * * *